United States Patent
Ortega et al.

(10) Patent No.: US 11,013,591 B2
(45) Date of Patent: May 25, 2021

(54) SYSTEMS AND METHODS WITH STENT AND FILLING STRUCTURE

(71) Applicant: Endologix LLC, Irvine, CA (US)

(72) Inventors: Carlos Ortega, Irvine, CA (US); Ryan Goff, Houston, TX (US); Aric Stone, Newport Beach, CA (US); Eric Noda, Rancho Santa Margarita, CA (US)

(73) Assignee: Endologix LLC, Irvine, CA (US)

( * ) Notice: Subject to any disclaimer, the term of this patent is extended or adjusted under 35 U.S.C. 154(b) by 0 days.

(21) Appl. No.: 15/774,511

(22) PCT Filed: Aug. 30, 2017

(86) PCT No.: PCT/US2017/049482
§ 371 (c)(1),
(2) Date: May 8, 2018

(87) PCT Pub. No.: WO2018/045097
PCT Pub. Date: Mar. 8, 2018

(65) Prior Publication Data
US 2020/0253710 A1  Aug. 13, 2020

Related U.S. Application Data

(60) Provisional application No. 62/382,207, filed on Aug. 31, 2016.

(51) Int. Cl.
*A61F 2/07* (2013.01)
*A61F 2/06* (2013.01)

(52) U.S. Cl.
CPC .......... *A61F 2/07* (2013.01); *A61F 2002/065* (2013.01); *A61F 2002/072* (2013.01); *A61F 2002/077* (2013.01); *A61F 2210/0085* (2013.01)

(58) Field of Classification Search
CPC .................................... A61F 2/06; A61F 2/07
(Continued)

(56) References Cited

U.S. PATENT DOCUMENTS 5,843,160 A    12/1998  Rhodes
7,842,069 B2 * 11/2010  Widomski ......... A61B 17/0057
                                                 606/213

(Continued)

FOREIGN PATENT DOCUMENTS

WO    WO-01/21108       3/2001
WO    WO-2015/183489 A1  12/2015
WO    WO-2017/117068 A1  7/2017

OTHER PUBLICATIONS

International Search Report and Written Opinion dated Nov. 21, 2017, from application No. PCT/US2017/049482.
(Continued)

*Primary Examiner* — Suzette J Gherbi
(74) *Attorney, Agent, or Firm* — Foley & Lardner LLP

(57) ABSTRACT

A system includes a filling structure deployable at least partially in a common iliac artery and an external iliac artery, and a scaffold positioned within a first lumen of the filling structure. The scaffold has a fenestration in a side of the scaffold that is positionable toward an internal iliac artery. The filling structure has a second lumen extending from the first lumen and positionable toward the internal iliac artery. A method includes deploying a filling structure at least partially in a common iliac artery and an external iliac artery and positioning a scaffold within a lumen of the filling structure such that a fenestration in a side of the scaffold is positioned toward an internal iliac artery.

24 Claims, 16 Drawing Sheets

(58) Field of Classification Search
USPC .................................................. 623/1.3–1.48
See application file for complete search history.

(56) References Cited

U.S. PATENT DOCUMENTS

| | | | |
|---|---|---|---|
| 8,945,200 B1 | 2/2015 | Eblacas et al. | |
| 10,022,249 B2* | 7/2018 | Evans | A61F 2/844 |
| 2002/0169497 A1 | 11/2002 | Wholey et al. | |
| 2003/0036745 A1 | 2/2003 | Khosravi et al. | |
| 2005/0182476 A1 | 8/2005 | Hartley et al. | |
| 2008/0294237 A1* | 11/2008 | Chu | A61F 2/07 |
| | | | 623/1.15 |
| 2009/0319029 A1* | 12/2009 | Evans | A61F 2/954 |
| | | | 623/1.35 |
| 2010/0036360 A1* | 2/2010 | Herbowy | A61M 25/10182 |
| | | | 604/500 |
| 2010/0106087 A1* | 4/2010 | Evans | A61B 17/12118 |
| | | | 604/103.03 |
| 2011/0196477 A1* | 8/2011 | Ganesan | A61F 2/07 |
| | | | 623/1.35 |
| 2012/0016456 A1* | 1/2012 | Herbowy | A61B 17/12118 |
| | | | 623/1.11 |
| 2012/0046684 A1 | 2/2012 | Evans et al. | |
| 2013/0053944 A1* | 2/2013 | Welch | A61F 2/954 |
| | | | 623/1.11 |
| 2013/0103135 A1* | 4/2013 | Vinluan | A61F 2/07 |
| | | | 623/1.13 |
| 2013/0204351 A1 | 8/2013 | Cox et al. | |
| 2018/0021045 A1* | 1/2018 | Deaton | A61F 2/07 |
| | | | 623/1.15 |
| 2018/0153680 A1* | 6/2018 | Greenberg | A61F 2/07 |
| 2019/0008631 A1* | 1/2019 | Stone | A61F 2/848 |
| 2019/0151070 A1* | 5/2019 | Chobotov | A61F 2/06 |
| 2019/0374225 A1* | 12/2019 | Schreck | A61B 6/504 |
| 2020/0324018 A1* | 10/2020 | Durali | C08F 222/1006 |

OTHER PUBLICATIONS

Extended European Search Report dated Mar. 9, 2020, from application No. 17847508.3.
International Preliminary Report and Patentability dated Mar. 14, 2019, from application No. PCT/US2017/049482.
Chinese Office Action dated Sep. 14, 2020, from application No. 201780066080.2.

* cited by examiner

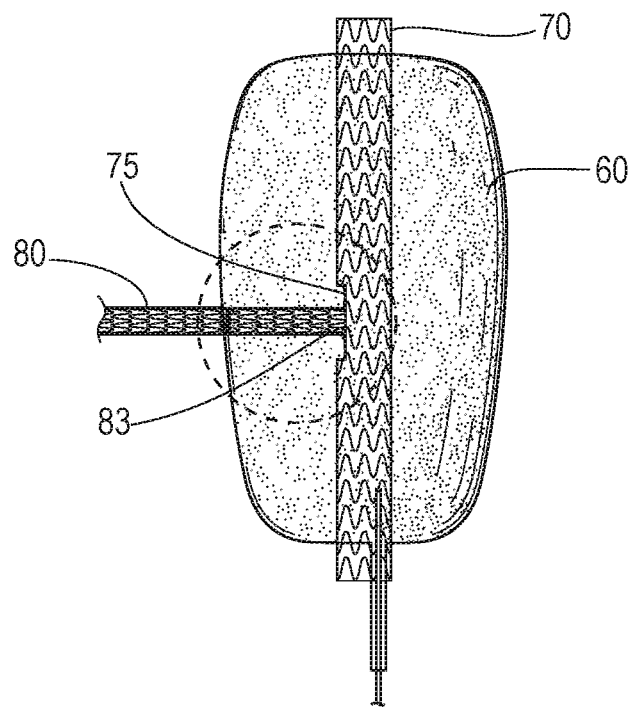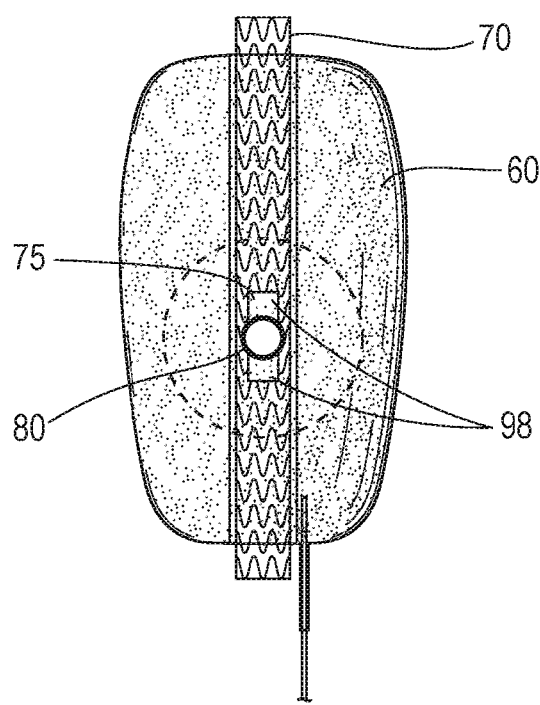
FIG. 14A  FIG. 15A
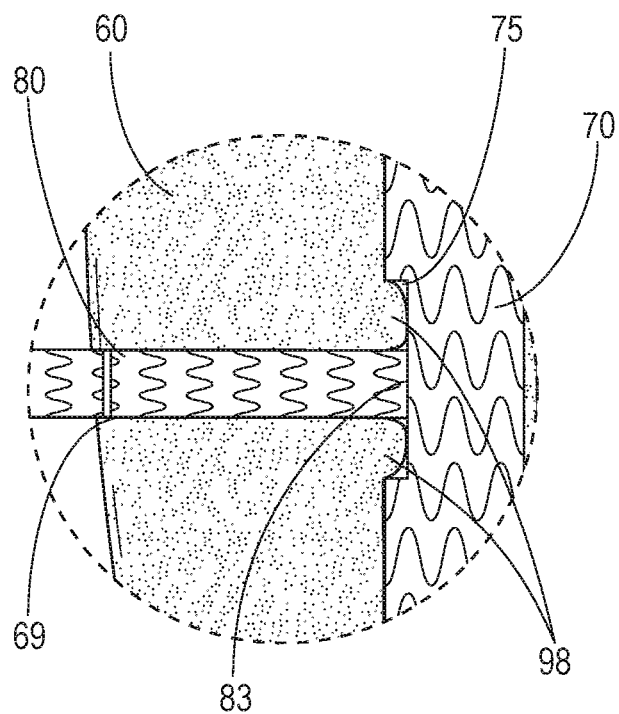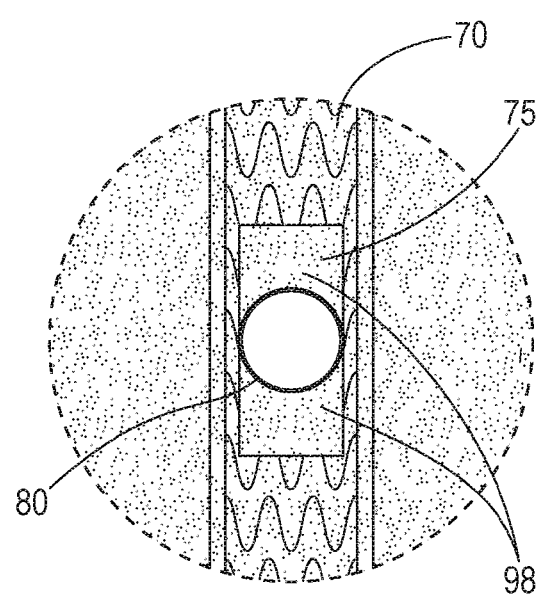
FIG. 14B  FIG. 15B

SYSTEMS AND METHODS WITH STENT AND FILLING STRUCTURE

CROSS-REFERENCE TO RELATED PATENT APPLICATION

This application claims priority from U.S. Provisional Patent Application No. 62/382,207, filed Aug. 31, 2016, the entire contents of which are incorporated by reference herein.

FIELD

Embodiments disclosed herein relate generally to systems with filling structures for use in blood vessels and to methods of using systems with filling structures in blood vessels. Various embodiments relate to expandable prosthesis and methods for treating aneurysms.

BACKGROUND

Aneurysms are enlargements or bulges in blood vessels that are often prone to rupture and which therefore present a serious risk to a patient. Aneurysms may occur in any blood vessel but are of particular concern when they occur in the cerebral vasculature or the patient's aorta.

Abdominal aortic aneurysms (AAA's) are classified based on their location within the aorta as well as their shape and complexity. Aneurysms that are found below the renal arteries are referred to as infrarenal abdominal aortic aneurysms. Suprarenal abdominal aortic aneurysms occur above the renal arteries. Thoracic aortic aneurysms (TAA's) occur in the ascending, transverse, or descending part of the upper aorta. Infrarenal aneurysms are the most common, representing about 70% of all aortic aneurysms. Suprarenal aneurysms are less common, representing about 20% of the aortic aneurysms. Thoracic aortic aneurysms are the least common and often the most difficult to treat.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. A common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Endoluminal grafts have recently come into widespread use for the treatment of aortic aneurysms in patients. In general, endoluminal repairs access the aneurysm "endoluminally" through either or both common iliac arteries. The grafts are then implanted. Successful endoluminal procedures have a much shorter recovery period than open surgical procedures.

Aneurysms also frequently occur in the iliac arteries in patients that have an abdominal aortic aneurysm. This has a reported prevalence of around 20-40% of AAA patients. In some patients, an aneurysm extends into an internal or external iliac artery.

SUMMARY OF THE DISCLOSURE

Various embodiments relate to systems including one or more filling structures and one or more stents for insertion into a blood vessel, and to methods of deploying such systems within one or more blood vessels. A system in accordance with an embodiment includes a filling structure deployable at least partially in a common iliac artery and an external iliac artery, and a scaffold positionable within a lumen of the filling structure. In various embodiments, the scaffold has a fenestration in a side of the scaffold that is positionable toward an internal iliac artery.

In various embodiments, the filling structure has a second lumen extending from the lumen and positionable toward the internal iliac artery. In some embodiments, the system further includes a second scaffold positionable within the second lumen. Also, in some embodiments, the second scaffold is insertable into the fenestration in the side of the scaffold.

In various embodiments, a first portion of the filling structure is configured to be located in at least a portion of the common iliac artery upon deployment of the filling structure, a second portion of the filling structure is configured to be located in at least a portion of the external iliac artery upon deployment of the filling structure, and a third portion of the filling structure is configured to be located in at least a portion of the internal iliac artery upon deployment of the filling structure.

In some embodiments, the lumen of the filling structure extends from a first end of the filling structure that is positionable to face an aorta to a second end of the filling structure that is positionable in the external iliac artery. In some embodiments, the filling structure has a second lumen extending from a side of the lumen to a third end of the filling structure that is positionable in the internal iliac artery.

In various embodiments, the system further includes a second scaffold insertable into the fenestration in the side of the scaffold. In some embodiments, the fenestration in the side of the scaffold is larger than an expanded diameter of the second scaffold. Also, in some embodiments, the filling structure is expandable to provide a seal around the second scaffold when the second scaffold is located within the fenestration in the side of the scaffold and the filling structure is inflated with a filling medium.

In various embodiments, the scaffold is attached to an inner surface of the lumen. In some embodiments, the filling structure has a second lumen extending from a side of the lumen and positionable toward the internal iliac artery, and the system further includes a second scaffold that is insertable into the fenestration in the side of the scaffold and that has a length that is greater than a length of the second lumen.

In some embodiments, the system further includes a radiopaque marker located next to the fenestration of the scaffold. In some embodiments, the system further includes a wire extendable through the fenestration in the side of the scaffold to the internal iliac artery. Also, in some embodiments, the system further includes a balloon that is inflatable within a second lumen of the filling structure and that is removable from the second lumen.

A method in accordance with various embodiments includes deploying a filling structure at least partially in a common iliac artery and an external iliac artery, and positioning a scaffold within a lumen of the filling structure such that a fenestration in a side of the scaffold is positioned toward an internal iliac artery. In various embodiments, the method further includes inserting a second scaffold into the fenestration in the side of the scaffold such that at least a portion of the second scaffold extends into the internal iliac artery.

In various embodiments, upon deployment of the filling structure, a first portion of the filling structure is located in at least a portion of the common iliac artery, a second portion of the filling structure is located in at least a portion of the external iliac artery, and a third portion of the filling structure is located in at least a portion of the internal iliac artery.

In some embodiments, the method further includes positioning a wire through the fenestration in the side of the scaffold and into the internal iliac artery. Also, in some embodiments the positioning of the wire is performed by a catheter passing over an aortic bifurcation.

A system in accordance with an embodiment includes a filling structure that is bifurcated. In various embodiments, the filling structure has a first lumen that extends from a first end to a second end of the filling structure, and the filling structure has a second lumen that extends from a side of the first lumen to a third end of the filling structure.

In some embodiments, the system further includes a first scaffold positioned in the first lumen of the filling structure and having a fenestration in a side of the first scaffold that is positioned toward the second lumen of the filling structure. Also, in some embodiments, the system further includes a second scaffold positioned in the second lumen of the filling structure and extending through the fenestration in the side of the first scaffold.

In various embodiments, a first portion of the filling structure is configured to be located in at least a portion of a common iliac artery upon deployment of the filling structure, a second portion of the filling structure is configured to be located in at least a portion of an external iliac artery upon deployment of the filling structure, and a third portion of the filling structure is configured to be located in at least a portion of an internal iliac artery upon deployment of the filling structure.

Various embodiments include a fenestrated and branched system or device with a filling structure, such as an endobag for deployment in at least portions of a common iliac artery, an external iliac artery, and an internal iliac artery. In various embodiments, a first scaffold is located within a lumen in the endobag and is extendable from the common iliac artery to the external iliac artery. In various embodiments, the first scaffold comprises a stent frame with an expanded Polytetrafluoroethylene (ePTFE) graft, which could be encapsulated or not, and is surrounded by the endobag. In various embodiments, the endobag is a single piece and has a bifurcated lumen, such that one lumen in the endobag surrounds the first scaffold, while a second lumen in the endobag allows for insertion of a second scaffold that is extendable from a fenestration in a side of the first scaffold to the internal iliac artery. In various embodiments, the second scaffold comprises a stent graft. In some embodiments, the endobag has a window or fenestration to allow for the second scaffold to extend from the fenestration in the side of the first scaffold to the internal iliac artery without having the endobag extend into the internal iliac artery.

An internal iliac segment of various embodiments is anchored with a balloon expandable stent that is part of the second scaffold. In some embodiments, this could be done with a self-expanding stent. Also, in some embodiments, rather than having a second scaffold, a balloon is used in an endobag branched segment lumen that is at least partially within an internal iliac artery to keep the lumen patent during polymer fill, and then the balloon is removable to allow the lumen created by the polymer filled endobag to provide blood flow to the internal iliac artery.

In various embodiments, the endobag is inflatable to seal around the branch of the scaffolds and around the second scaffold that acts as an anchoring stent, such that the endobag would seal any gutters around the stents and seal an aneurysm in the iliac artery. In various embodiments, the device is docked into a second device that repairs an aneurysm in the aorta. In various embodiments, a device in accordance with an embodiment is deployable first in an iliac artery and then an extending second device is deployable in an abdominal aortic aneurysm space, if needed, to seal an entire aneurysmal space. In some embodiments, the second device is deployable first in the abdominal aortic aneurysm space and then the device of an embodiment is deployable in the iliac artery as an extension to seal an entire aneurysmal space.

A device in accordance with various embodiments is deployable unilaterally in portions of a common iliac artery, an external iliac artery, and an internal iliac artery on one side of a patient, and various devices in accordance with various embodiments are deployable bilaterally such that there would be a corresponding device on both side of the patient in the respective portions of the common iliac arteries, the external iliac arteries, and the internal iliac arteries.

A method for deploying a device in accordance with an embodiment allows for the device to be deployed by advancing through femoral access on the side of the patient that is to be treated. From there the device in various embodiments is tracked up to the aneurysmal segment and unsheathed. In various embodiments the first scaffold in the device includes a self-expanding stent, so this would deploy the main stent that is part of the first scaffold. In some embodiments, the first scaffold is balloon expandable, and after unsheathing the balloon inflation would occur to expand a stent that is part of the first scaffold.

In various embodiments, the device includes a pre-cannulated wire through the window or fenestration in the first scaffold at the branch, and the fenestration is positionable toward the internal iliac artery. In various embodiments of the method for deployment, the wire is placed into the internal iliac artery with the use of pre-curved or steerable catheters. In some embodiments, the positioning of the wire is performed via access through the ipsilateral side from the external iliac artery. In some embodiments, the positioning of the wire is performed via access through the contralateral side by going over the aortic bifurcation. In various embodiments, the anatomy of the patient would determine the approach as to whether to access through the ipsilateral or contralateral side. In some embodiments there are two pre-cannulated wires going in opposite directions of the fenestration to accommodate both approaches. In such embodiments, the wire not being used could simply be removed prior to putting the device in the patient.

In various embodiments of the method for deployment, once the internal iliac artery is cannulated, a sheath is placed into the internal iliac artery. Then in various embodiments an anchoring stent, such as a stent of the second scaffold, is tracked to the target location that is at least partially in the internal iliac artery by passing through the fenestration in the first scaffold. For a balloon expandable system or device, in various embodiments the balloons would all be inflated using a kissing balloon technique. For a self-expanding system or device, in various embodiments balloons are tracked and inflated in a kissing balloon technique fashion. In various embodiments, the balloons protect and preserve the lumen during endobag fill. In various embodiments, the stents are made with enough radial force to withstand the fill pressures of the endobag such that balloons are not necessary.

In various embodiments, the method of deployment further includes pre-fill of the endobag, such as with a saline solution, and then evacuation of the saline solution, and then polymer fill of an interior volume of the endobag. In some embodiments, an optional secondary fill of the endobag is performed. In some embodiments, a fill line for the endobag has a "pipe cleaner" that could be removed and inserted multiple times to allow for more than two fillings of the endobag.

BRIEF DESCRIPTION OF THE DRAWINGS

FIG. 14A illustrates another view of the system of FIG. 10 in accordance with an embodiment.

FIG. 14B illustrates a portion of the system of the FIG. 14A shown by a dotted circle in FIG. 14A.

FIG. 15A illustrates another view of the system of FIG. 10 in accordance with an embodiment.

FIG. 15B illustrates a portion of the system of the FIG. 15A shown by a dotted circle in FIG. 15A.

DETAILED DESCRIPTION

Figure 1:
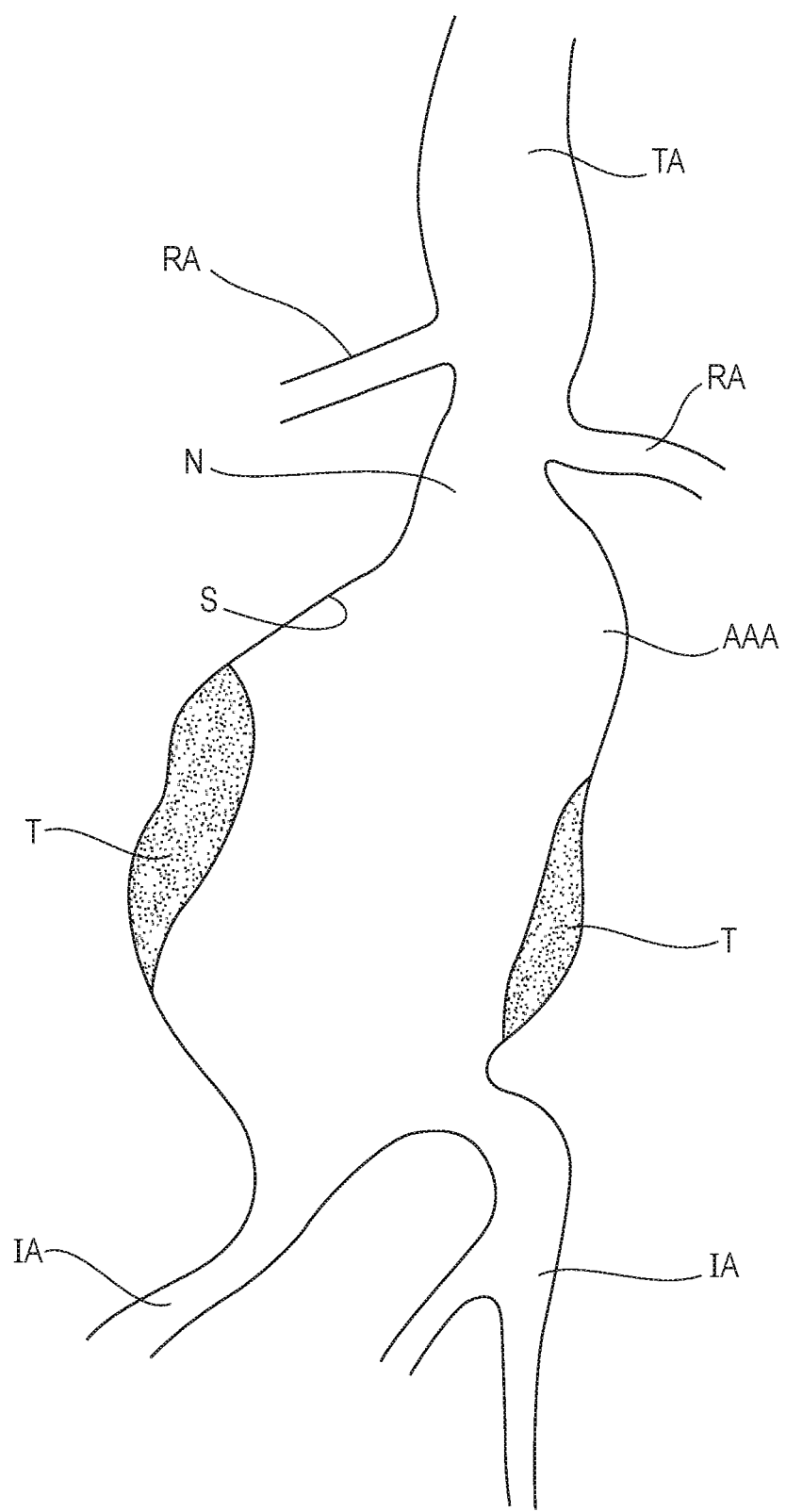
FIG. 1 illustrates an anatomy of a patient with an example infrarenal abdominal aortic aneurysm.

Referring now to FIG. 1, the anatomy of an infrarenal abdominal aortic aneurysm is illustrated. The thoracic aorta (TA) has renal arteries (RA) at its distal end above the common iliac arteries (IA). The abdominal aortic aneurysm (AAA) typically forms between the renal arteries (RA) and the common iliac arteries (IA) and may have regions of mural thrombus (T) over portions of its inner surface (S). The space between the renal arteries and an upper end of the abdominal aortic aneurysm is typically referred to as a neck area (N) of the aneurysm.

Figure 2:
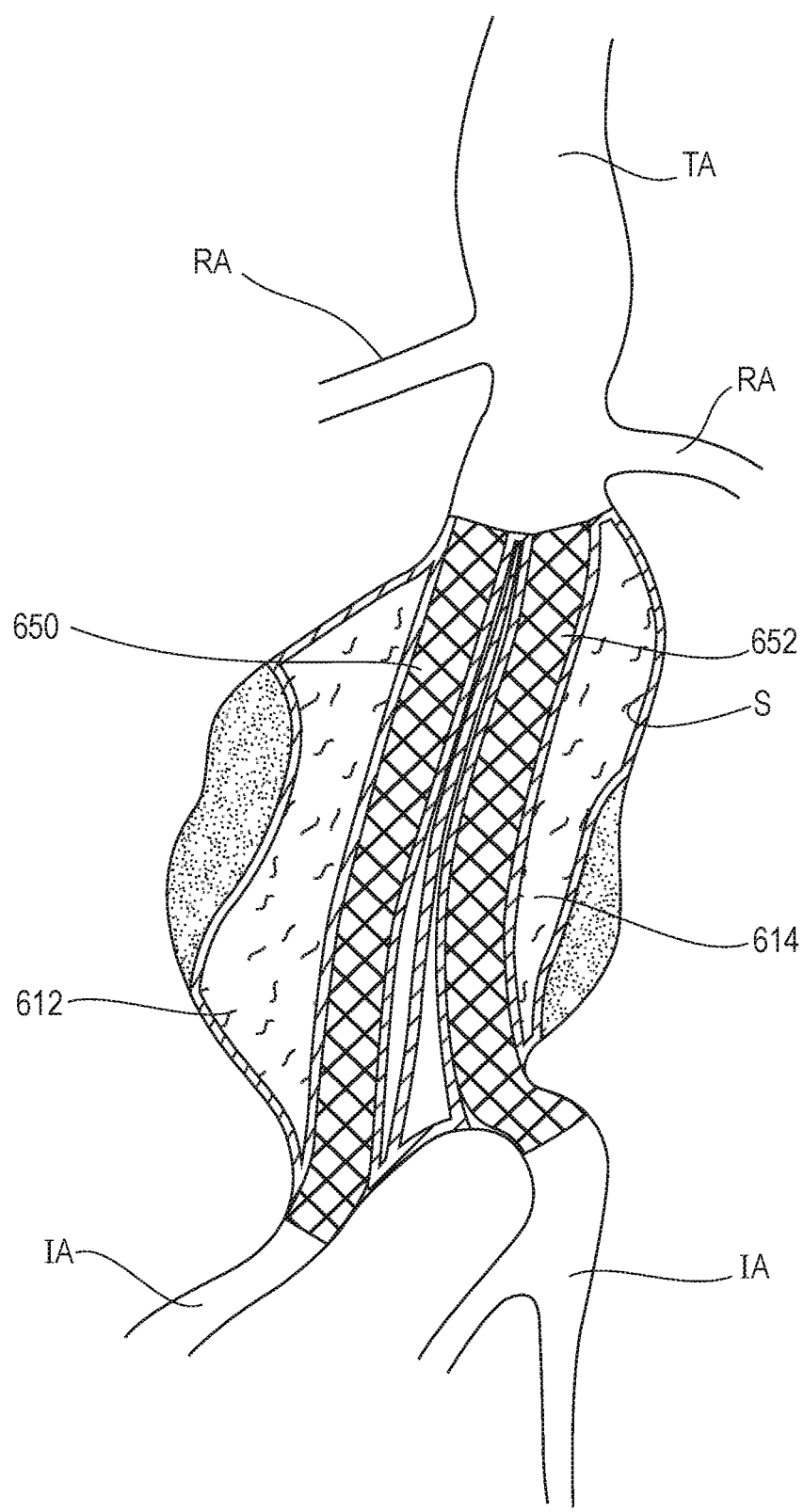
FIG. 2 illustrates a system having one or more filling structures and scaffolds for use in an aneurysm.

A type of graft system having filling structures supported by scaffolds for use in an aneurysm is illustrated in FIG. 2, which is a figure from U.S. Pat. No. 8,870,941, titled "Graft Systems Having Filling Structures Supported By Scaffolds And Methods For Their Use," issued Oct. 28, 2014, the entire contents of which are incorporated by reference herein. With reference to FIG. 2, a first filling structure 612 and a second filling structure 614 are inserted into an infrarenal abdominal aortic aneurysm. The first filling structure 612 and the second filling structure 614 are filled with filling medium or material that is cured or otherwise hardened. The hardened filling structures 612 and 614 then each provide a tubular lumen opening from a location near an upper end of the aneurysm beneath the renal arteries to a respective common iliac artery.

Referring to FIG. 2, a first scaffold 650 is placed in the tubular lumen of the first filling structure 612 while a second scaffold 652 is placed in the tubular lumen of the second filling structure 614. The first and second scaffolds 650 and 652 are generally stent-like and/or graft-like vascular structures that each extend from a location near an upper end of the aneurysm that is beneath the renal arteries into a respective common iliac artery. The first scaffold 650 and the second scaffold 652 each provide a lumen for blood flow across the aneurysm into a respective common iliac artery.

Figure 3:
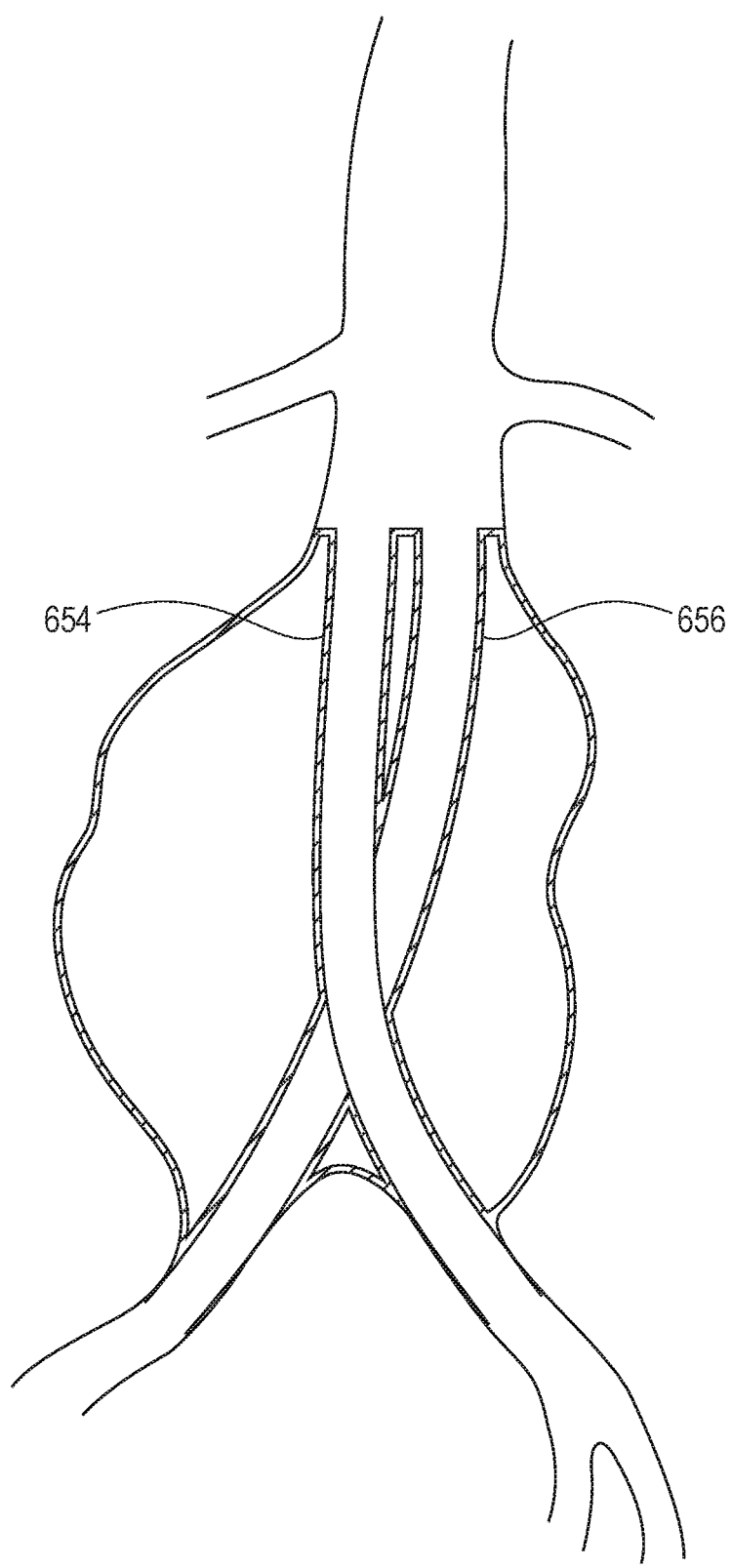
FIG. 3 illustrates a system having scaffolds for use in an aneurysm in which the scaffolds cross around each other.

In FIG. 2, the lumen created by the first filling structure 612 and the lumen created by the second filling structure 614 are generally parallel to each other, such that the first scaffold 650 and the second scaffold 652 are generally parallel to each other. As illustrated in FIG. 3, it is also possible to have a first scaffold 654 cross around a second scaffold 656. Some examples of scaffolds that cross are shown in U.S. Patent App. Pub. No. 2009/0319029, titled "Docking Apparatus And Methods Of Use," published Dec. 24, 2009, the entire contents of which are incorporated by reference herein.

Figure 4:
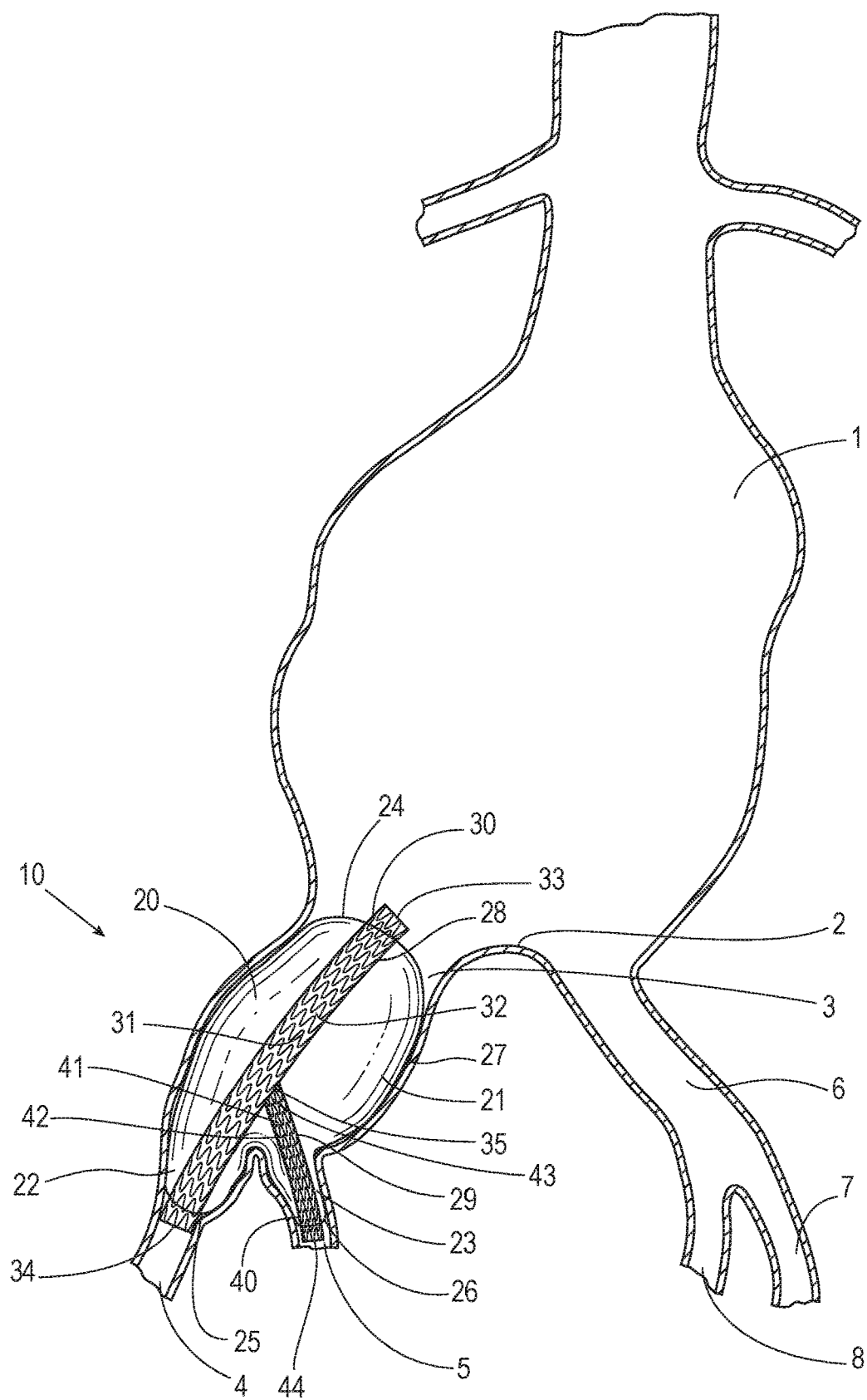
FIG. 4 illustrates a system in accordance with an embodiment deployed in at least portions of a common iliac artery, an external iliac artery, and an internal iliac artery to seal at least a portion of an aneurysm.

Aneurysms also frequently occur in the iliac arteries in patients that have an abdominal aortic aneurysm. This has a reported prevalence of around 20-40% of AAA patients. In some patients, an aneurysm extends into an internal or external iliac artery. FIG. 4 illustrates a system 10 in accordance with an embodiment deployed in at least portions of a common iliac artery 3, an external iliac artery 4, and an internal iliac artery 5 to seal at least a portion of an aneurysm. The anatomy of a patient in FIG. 4 includes an aorta 1, an aortic bifurcation 2, the common iliac artery 3, the external iliac artery 4, the internal iliac artery 5, a common iliac artery 6, an external iliac artery 7, and an internal iliac artery 8. The common iliac arteries 3 and 6 are two arteries that originate from the aortic bifurcation 2. The common iliac artery 3 bifurcates into the external iliac artery 4 and the internal iliac artery 5. The common iliac artery 6 bifurcates into the external iliac artery 7 and the internal iliac artery 8. The aneurysm shown in FIG. 4 is shown to occur in the aorta 1 and to extend at least partially into the common iliac artery 3, the external iliac artery 4, and the internal iliac artery 5.

In various embodiments, the device or system 10 allows for sealing at least a portion of the aneurysm in at least portions of the common iliac artery 3, the external iliac artery 4, and the internal iliac artery 5. While the system 10 is shown in FIG. 4 on one side of the patient, it should be understood that the system 10 could also be used in the common iliac artery 6, the external iliac artery 7, and the internal iliac artery 8. Also in various embodiments, two of the system 10 may be provided such that one system 10 is provided for the common iliac artery 3, the external iliac artery 4, and the internal iliac artery 5, while another system 10 is provided for the common iliac artery 6, the external iliac artery 7, and the internal iliac artery 8.

Figure 5:
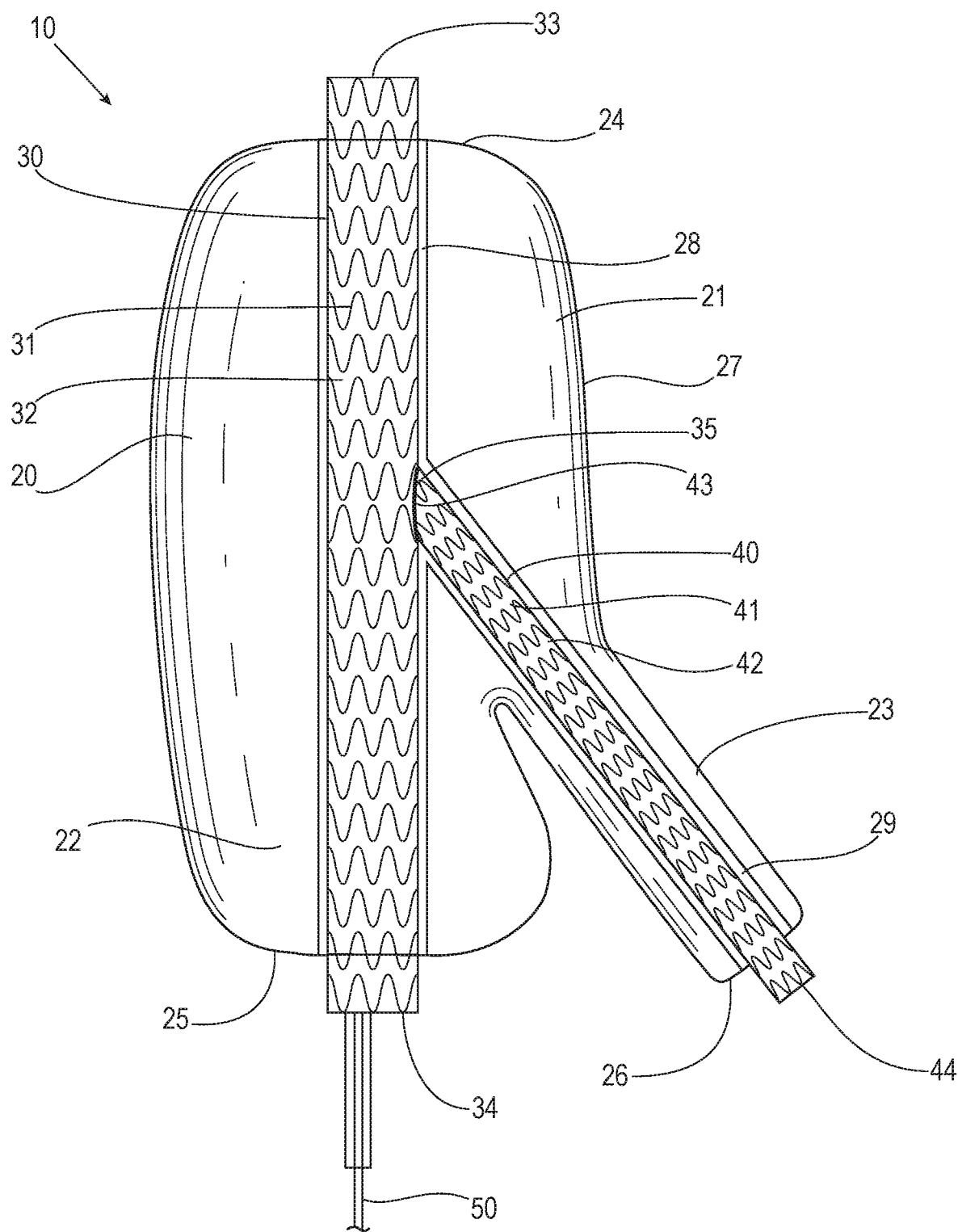
FIG. 5 illustrates the system of FIG. 4 in accordance with an embodiment including a filling structure having a portion that is expandable into at least a portion of an internal iliac artery.
Figure 6:
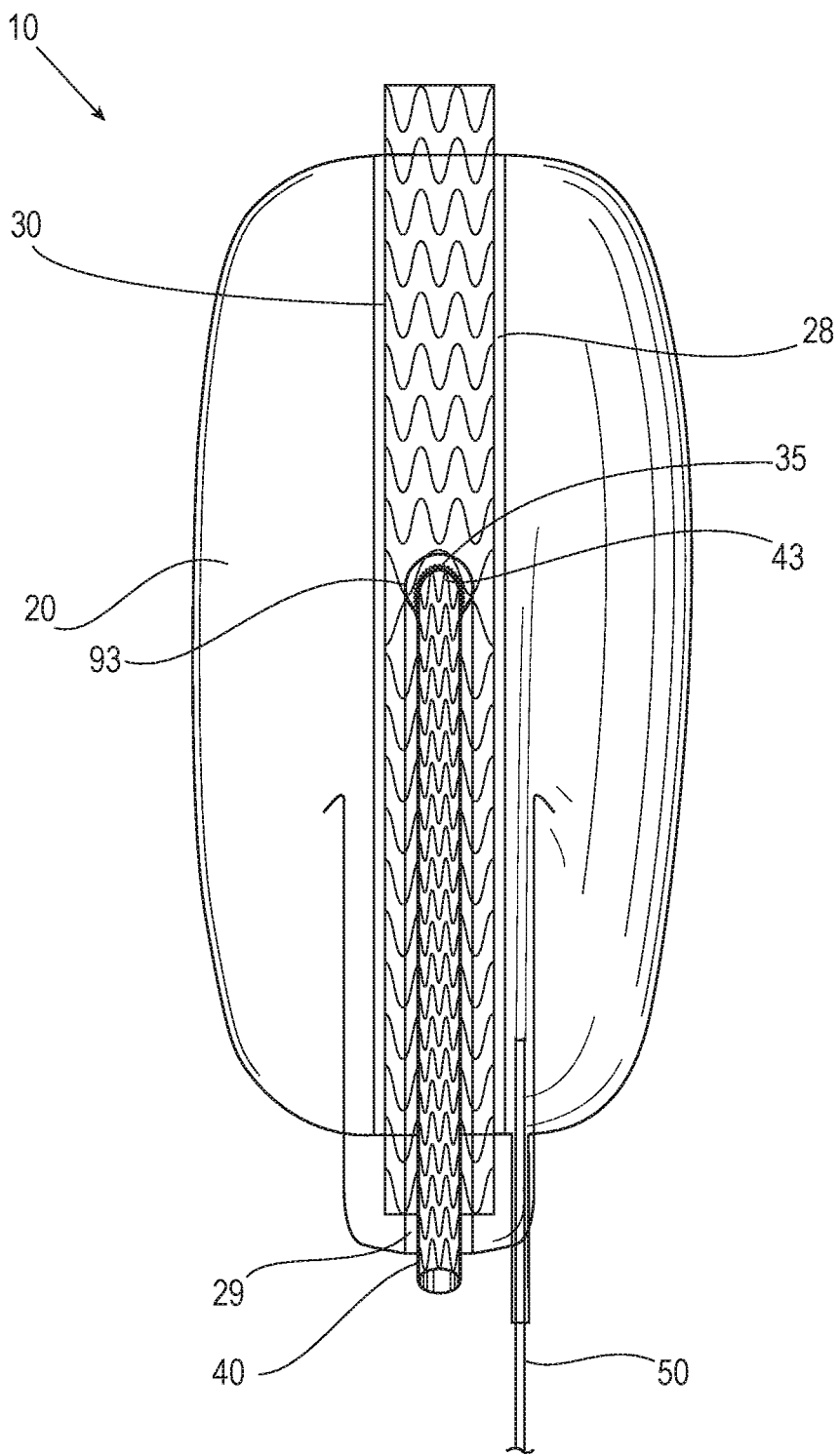
FIG. 6 illustrates another view of the system of FIG. 5 in accordance with an embodiment.
Figure 7:
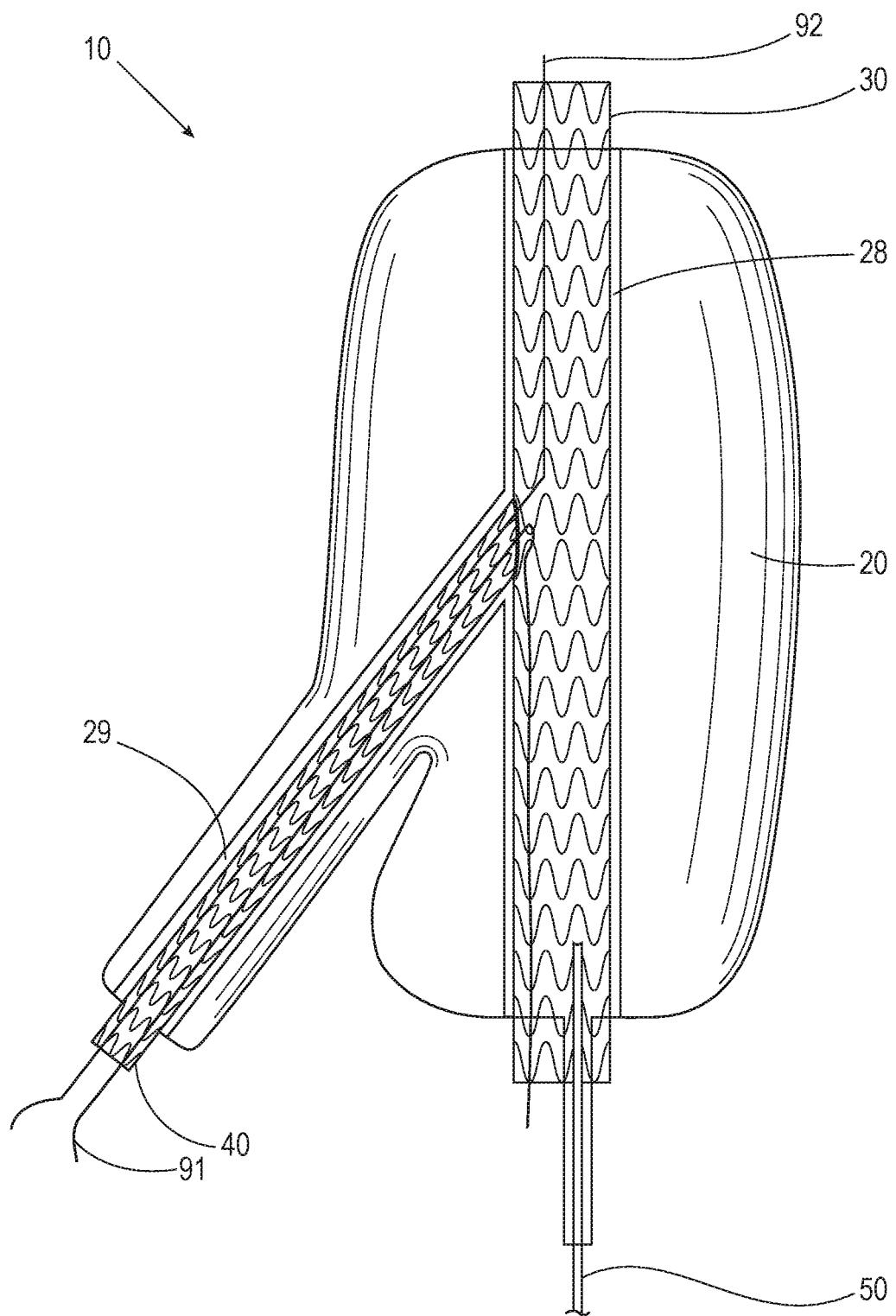
FIG. 7 illustrates yet another view of the system of FIG. 5 in accordance with an embodiment.

FIG. 5 illustrates the system 10 of FIG. 4 in accordance with an embodiment. FIG. 6 illustrates another view of the system 10 of FIG. 5 in accordance with an embodiment. FIG. 7 illustrates yet another view of the system 10 of FIG. 5 in accordance with an embodiment including wires 91 and 92. With reference to FIGS. 4, 5, 6, and 7, the system 10 includes a filling structure 20, a first scaffold 30, a second scaffold 40, and a fill tube 50. In various embodiments, the filling structure 20 is bifurcated. A first portion 21 of the filling structure 20 is configured and shaped to be located in at least a portion of the common iliac artery 3 upon deployment. A second portion 22 of the filling structure 20 is configured and shaped to be located in at least a portion of the external iliac artery 4 upon deployment. A third portion 23 of the filling structure 20 is configured and shaped to be located in at least a portion of the internal iliac artery 5 upon deployment.

In various embodiments, upon deployment, a first end 24 of the filling structure 20 faces the aorta 1, a second end 25 of the filling structure 20 is located in the external iliac artery 4, and a third end 26 of the filling structure 20 is located in the internal iliac artery 5. The filling structure 20 has an outer wall 27. In various embodiments, the filling structure 20 includes a first lumen 28 in the filling structure 20 that is defined by a first inner wall of the filling structure 20. Also, in various embodiments, the filling structure 20 includes a second lumen 29 in the filling structure 20 defined by a second inner wall of the filling structure 20.

The filling structure 20 is inflatable with a filling medium or material from an uninflated state to an inflated state. The first lumen 28 extends from the first end 24 of the filling structure 20 to the second end 25 of the filling structure 20. The second lumen 29 extends from a side of the first lumen 28 of the filling structure 20 to the third end 26 of the filling structure 20. In various embodiments, the filling structure 20 comprises an endobag with the first lumen 28 and the second lumen 29.

In some embodiments, the filling structure 20 is partially or completely formed from a generally noncompliant material. In some embodiments, the filling structure 20 is an expanded Polytetrafluoroethylene (ePTFE) sealed bag that is coated on the inside with polyurethane. An internal volume of the filling structure 20 is surrounded by the outer wall 27. In various embodiments, the first lumen 28 is cylindrically shaped with an open top and an open bottom. In various embodiments, the second lumen 29 is cylindrically shaped with an open top into the first lumen 28 and an open bottom.

In various embodiments, the filling structure 20 is fillable with a hardenable filling material such as Polyethylene glycol (PEG) or another polymer that may be polymerized in situ. In various embodiments, the filling structure 20 is fillable via the fill tube 50 that is detachable from the filling structure 20. In various embodiments, the filling structure 20 includes at least one valve at an end of the fill tube 50 to permit the introduction of the filling material or medium into the internal volume of the filling structure 20. In various embodiments, the valve is a simple flap valve. Other more complex ball valves, and other one-way valve structures may be provided. In other instances, two-way valve structures may be provided to permit both filling and selective emptying of the internal volume of the filling structure 20. In some instances, the fill tube 50 comprises a needle or other filling element to pass through a valve to permit both filling and removal of filling medium from the filling structure 20.

In some embodiments, various internal and external surfaces of the filling structure 20 are shaped, coated, treated, or otherwise modified, to provide for a number of particular features. For example, in some embodiments, the outer wall 27 is shaped to have rings, stipples, or other surface features formed into the material of the filling structure 20 at the time of molding, vapor deposition, or other manufacturing process. In some embodiments, an outer surface of the outer wall 27 is coated with one or more materials, such as adhesives, drugs, active substances, fibers, flocking, foams, or a variety of other materials. Such surface features or modifications allow for enhancing sealing or attachment of the outer wall 27 to an inner surface of a blood vessel being treated. In various embodiments, upon inflation of the filling structure 20 with the filling medium, the outer wall 27 expands to contact surfaces of one or more blood vessels.

In various embodiments, an inner surface of the outer wall 27 of the filling structure 20 is modified by providing features, coatings, surface roughening, or a variety of other modifications. Such internal features allow for enhancing adherence of the inner surface of the outer wall 27 to the filling material or medium as the filling medium is cured or otherwise hardened in the internal volume of the filling structure 20. In some instances, materials may be coated on all or a portion of the inside surface of the outer wall 27 to induce or catalyze hardening of the filling medium as it is being introduced into the filling structure 20.

In various embodiments, the first scaffold 30 comprises a stent 31 and a graft 32, such that it is a stent graft. The first scaffold 30 has a first end 33 and a second end 34. The first scaffold 30 also has a fenestration 35 in the stent 31 and graft 32 of the first scaffold 30 to allow for insertion of the second scaffold 40. In various embodiments, the first scaffold 30 has a cylindrical shape with an open top and an open bottom to form a lumen. In various embodiments, the first scaffold 30 is attached to an inner surface of the first lumen 28 of the filling structure 20. In some embodiments, the first scaffold 30 comprises the stent 31 and, in some embodiments, the first scaffold 30 comprises the stent 31 with the graft 32 covering the stent 31. In some embodiments, the stent 31 is made from cobalt-chromium (CoCr) alloy, stainless steel, nitinol, or the like, and in some embodiments the graft 32 comprises a polymer cover, such as ePTFE, or the like, that is applied to the stent 31 as the graft 32.

In various embodiments, the second scaffold 40 comprises a stent 41 and a graft 42, such that it is a stent graft. The second scaffold 40 has a first end 43 and a second end 44. In various embodiments, the second scaffold 40 has a cylindrical shape with an open top and an open bottom to form a lumen. The filling structure 20 is inflatable or expandable, and when it expands, the second lumen 29 is revealed. In various embodiments, the second scaffold 40 is positionable within the second lumen 29 of the filling structure 20 to extend from the fenestration 35 in the first scaffold 30. In some embodiments, the second scaffold 40 comprises the stent 41 and, in some embodiments, the second scaffold 40 comprises the stent 41 with the graft 42 covering the stent 41. In some embodiments, the stent 41 is made from cobalt-chromium (CoCr) alloy, stainless steel, nitinol, or the like, and in some embodiments the graft 42 comprises a polymer cover, such as ePTFE, or the like, that is applied to the stent 41 as the graft 42.

In various embodiments, the filling structure 20 and/or the first scaffold 30 further includes a radiopaque marker 93 and the one or more wires 91, 92. In various embodiments, the radiopaque marker 93 is assembled next to the fenestration 35 of the first scaffold 30 to aid in locating the fenestration 35 and the second lumen 29 for insertion of the second scaffold 40 when the filling structure 20 is in the body of a patient. The radiopaque marker 93 in various embodiments indicates a location of the fenestration 35. In some embodiments, the radiopaque marker 93 is a thin-walled metal tube providing for visibility under an x-ray fluoroscope and is made from a high density metal, such as platinum, gold, tantalum, or the like. In some embodiments, the second lumen 29 and/or the fenestration 35 is pre-wired with the one or more wires 91, 92, such as a pre-cannulated wire through the fenestration 35 that is positionable within the internal iliac artery 5 with the use of precurved or steerable catheters. In some embodiments, the positioning of the wire 91 is performed via access through the ipsilateral side from the external iliac artery 4. In some embodiments, the positioning of the wire 92 is performed via access through the contralateral side by going over the aortic bifurcation 2. In various embodiments, the anatomy of the patient would determine the approach as to whether to access through the ipsilateral or contralateral side. In some embodiments there are two pre-cannulated wires 91, 92 going in opposite directions from the fenestration 35 to accommodate both approaches. In such embodiments, the wire not being used could simply be removed prior to putting the system 10 in the patient.

A method for deploying the system 10 includes inserting a guide wire through a puncture in the patient's groin to access the external iliac artery 4 and to move the guide wire up through the common iliac artery 3. In various embodiments, a delivery catheter is used to deliver the filling structure 20 with the first scaffold 30 that is attached to the inner surface of the first lumen 28 of the filling structure 20. In various embodiments, the catheter includes a catheter shaft with a balloon near its distal end. In some embodiments, the first scaffold 30, which is radially expandable, is positioned over the balloon, and the filling structure 20 is disposed over the first scaffold 30 since the first scaffold 30 is located within the first lumen 28. In some embodiments, the first scaffold 30 is self-expandable and there is no need for a separate balloon for expansion. In various embodiments, the catheter further comprises a guide wire lumen for following the guide wire. In various embodiments, the catheter is also connected to the fill tube 50 for delivering a filling medium or material to the internal volume of the filling structure 20.

In various embodiments, the balloon is initially in an uninflated state. The first scaffold 30 is initially in an unexpanded state on the balloon. The filling structure 20 is initially in an uninflated state with the first scaffold 30 in the unexpanded state at least partially within the first lumen 28.

In various embodiments, the catheter with the filling structure 20 in the uninflated state and the first scaffold 30 in the unexpanded state is advanced over the guide wire. In some embodiments, the first scaffold 30 is self-expandable, and rather than using a balloon, the catheter includes a sheath to surround the first scaffold 30 and the filling structure 20, and the sheath can be retracted to allow for the first scaffold 30 to expand.

In various embodiments, the device includes a pre-cannulated wire, such as the wire 91 or the wire 92, through the window or fenestration 35 in the first scaffold 30 at the branch, and the fenestration 35 is positionable toward the internal iliac artery 5. In various embodiments of the method for deployment, the wire is placed into the internal iliac artery 5 with the use of pre-curved or steerable catheters. In some embodiments, the positioning of the wire 91 is performed via access through the ipsilateral side from the external iliac artery 4. In some embodiments, the positioning of the wire 92 is performed via access through the contralateral side by going over the aortic bifurcation 2. In various embodiments, the anatomy of the patient would determine the approach as to whether to access through the ipsilateral or contralateral side.

In various embodiments, once the internal iliac artery 5 is cannulated, a sheath is placed into the internal iliac artery 5. Then in various embodiments the second scaffold 40 is tracked to the target location that is at least partially in the internal iliac artery 5 by passing through the fenestration 35 in the first scaffold 30 to position the second scaffold 40 at least partially in the second lumen 29 of the filling structure 20. For a balloon expandable system 10, in various embodiments the second scaffold 40 surrounds a second balloon and the balloons would all be inflated using a kissing balloon technique. In various embodiments, the balloons protect and preserve the first lumen 28 and the second lumen 29 during filling of the filling structure 20. In various embodiments, the stent 31 and the stent 41 are made with enough radial force to withstand the fill pressures of the filling structure 20 such that balloons are not necessary for deployment.

In various embodiments, the method of deployment further includes pre-fill of the filling structure 20, such as with a saline solution, and then evacuation of the saline solution, and then polymer fill of an interior volume of the filling structure 20. In some embodiments, an optional secondary fill of the filling structure 20 is performed. In some embodiments, the fill tube 50 for the filling structure 20 has a "pipe cleaner" that is removable and insertable multiple times to allow for more than two fillings of the filling structure 20. In various embodiments, the saline solution can be introduced into the internal volume of the filling structure 20 through the fill tube 50 to unfurl the filling structure 20. The saline solution can then be withdrawn through the fill tube 50, and the filling structure 20 is filled with a hardenable filling medium or material such as PEG or another polymer that may be polymerized in situ. In various embodiments, the filling medium is able to cure or harden in place. It may be desirable to monitor pressure of the filling medium or material as it fills the filling structure 20 and/or the volume of filling medium or material introduced into the filling structure 20. The hardenable filling medium is used to fill the filling structure 20 to cause an outer surface of the filling structure 20 to expand and create a seal with an inner surface of one or more blood vessels.

Any balloons can then be deflated and removed along with the catheter shaft and the guide wire, which opens a lumen through the first scaffold 30 to allow for blood to flow from the aorta 1 through the first scaffold 30 to the external iliac artery 4. A lumen is also open through the second scaffold 40 to allow blood to flow from the aorta 1, through a portion of the first scaffold 30, through the fenestration 35 in the first scaffold 30, and through the second scaffold 40 to the internal iliac artery 5.

In various embodiments, upon deployment the first portion 21 of the filling structure 20 is located in at least a portion of the common iliac artery 3, the second portion 22 of the filling structure 20 is located in at least a portion of the external iliac artery 4, and the third portion 23 of the filling structure 20 is located in at least a portion of the internal iliac artery 5. Also, upon deployment in various embodiments, the first end 33 of the first scaffold 30 is positioned to accept blood from the aorta 1, the second end 34 of the first scaffold 30 is positioned in the external iliac artery 4 to deliver blood to the external iliac artery 4, the fenestration 35 of the first scaffold 30 faces the internal iliac artery 5, the first end 43 of the second scaffold 40 is positioned within the fenestration 35 of the first scaffold 30, and the second end 44 of the second scaffold 40 is positioned in the internal iliac artery 5 to deliver blood to the internal iliac artery 5.

Figure 8:
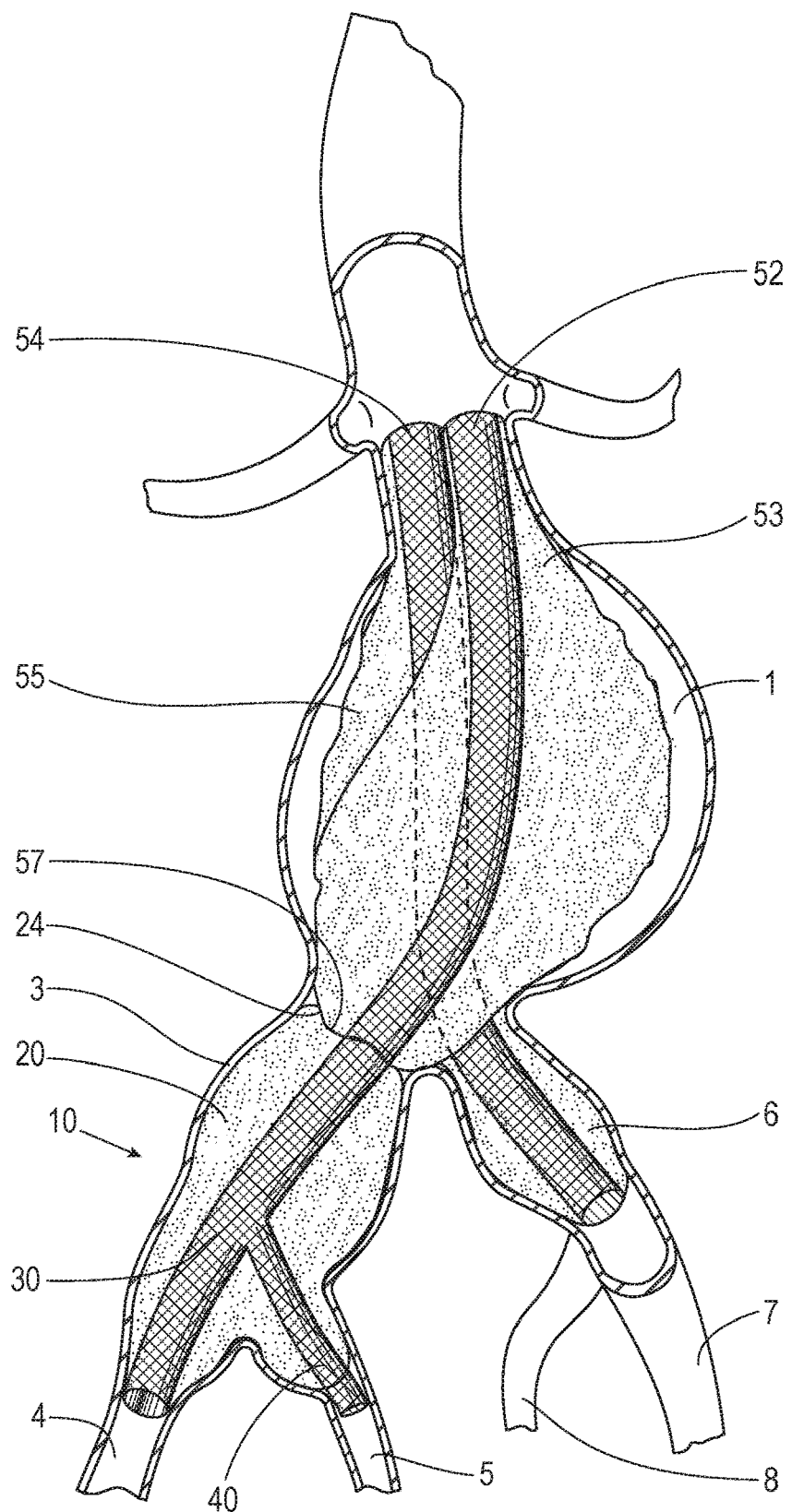
FIG. 8 illustrates an example deployment of the system of FIG. 4 in accordance with an embodiment that interfaces with another system to seal an aneurysm.

With reference to FIG. 8, the system 10 with the filling structure 20, the first scaffold 30, and the second scaffold 40 can be used in various embodiments as an extender for another system used to repair an AAA in the aorta 1 with a scaffold 52, a filling structure 53, a scaffold 54, and a filling structure 55. In various embodiments, the system 10 is implanted in at least portions of the common iliac artery 3, the external iliac artery 4 and the internal iliac artery 5 to seal a portion of the aneurysm that extends down into those blood vessels from the aorta 1. In various embodiments, a portion of the first scaffold 30 is mated with the scaffold 52 to allow for continuous blood flow from the scaffold 52 to the first scaffold 30. Also, in various embodiments, the first end 24 of the filling structure 20 abuts an end 57 of the filling structure 53.

Figure 9:
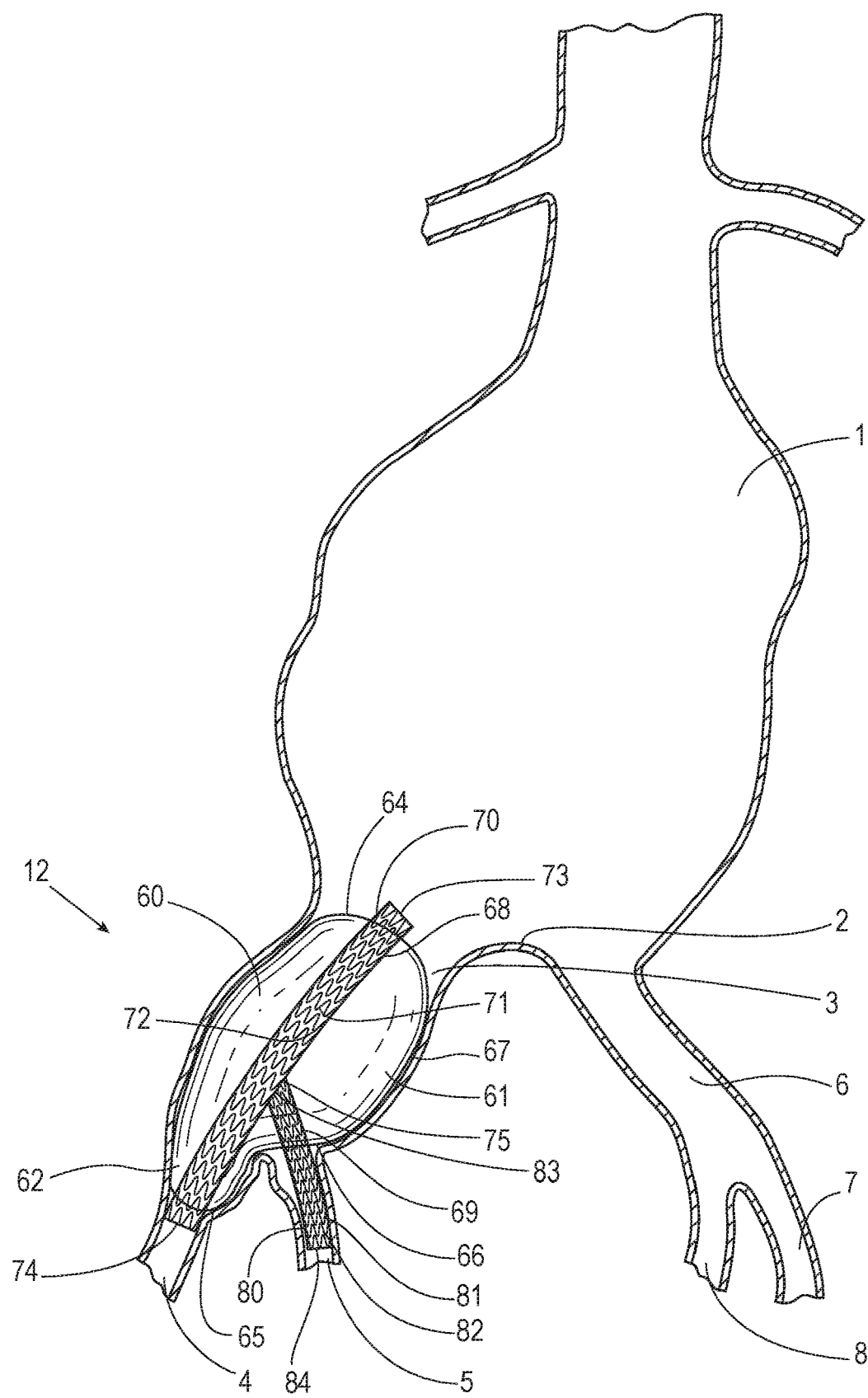
FIG. 9 illustrates a system in accordance with an embodiment deployed in at least portions of a common iliac artery, an external iliac artery, and an internal iliac artery to seal at least a portion of an aneurysm.

FIG. 9 illustrates a system 12 in accordance with an embodiment deployed in at least portions of the common iliac artery 3, the external iliac artery 4, and the internal iliac artery 5 to seal at least a portion of an aneurysm. The anatomy of a patient in FIG. 9 includes the aorta 1, the aortic bifurcation 2, the common iliac artery 3, the external iliac artery 4, the internal iliac artery 5, the common iliac artery 6, the external iliac artery 7, and the internal iliac artery 8. The common iliac arteries 3 and 6 are two arteries that originate from the aortic bifurcation 2. The common iliac artery 3 bifurcates into the external iliac artery 4 and the internal iliac artery 5. The common iliac artery 6 bifurcates into the external iliac artery 7 and the internal iliac artery 8. The aneurysm shown in FIG. 9 is shown to occur in the aorta 1 and to extend at least partially into the common iliac artery 3, the external iliac artery 4, and the internal iliac artery 5.

In various embodiments, the device or system 12 allows for sealing at least a portion of the aneurysm in at least portions of the common iliac artery 3 and the external iliac artery 4, and allows for blood flow into the external iliac artery 4 and the internal iliac artery 5. While the system 12 is shown in FIG. 9 on one side of the patient, it should be understood that the system 12 could also be used in the common iliac artery 6, the external iliac artery 7, and the internal iliac artery 8. Also in various embodiments, two of the system 12 may be provided such that one system 12 is provided for the common iliac artery 3, the external iliac artery 4, and the internal iliac artery 5, while another system 12 is provided for the common iliac artery 6, the external iliac artery 7, and the internal iliac artery 8.

Figure 10:
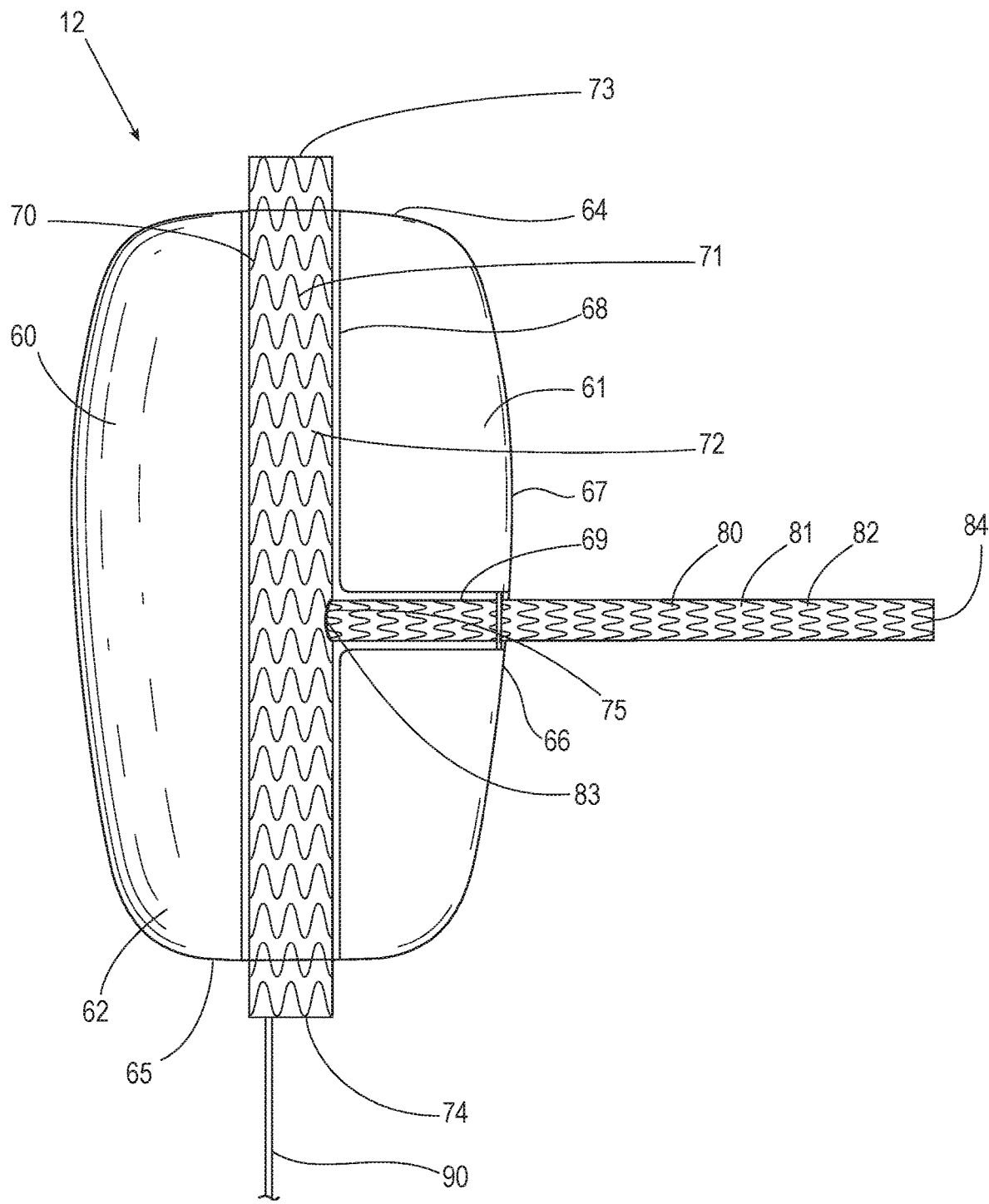
FIG. 10 illustrates the system of FIG. 9 in accordance with an embodiment including a filling structure with an opening that is positioned to allow a scaffold to extend into at least a portion of an internal iliac artery.
Figure 11:
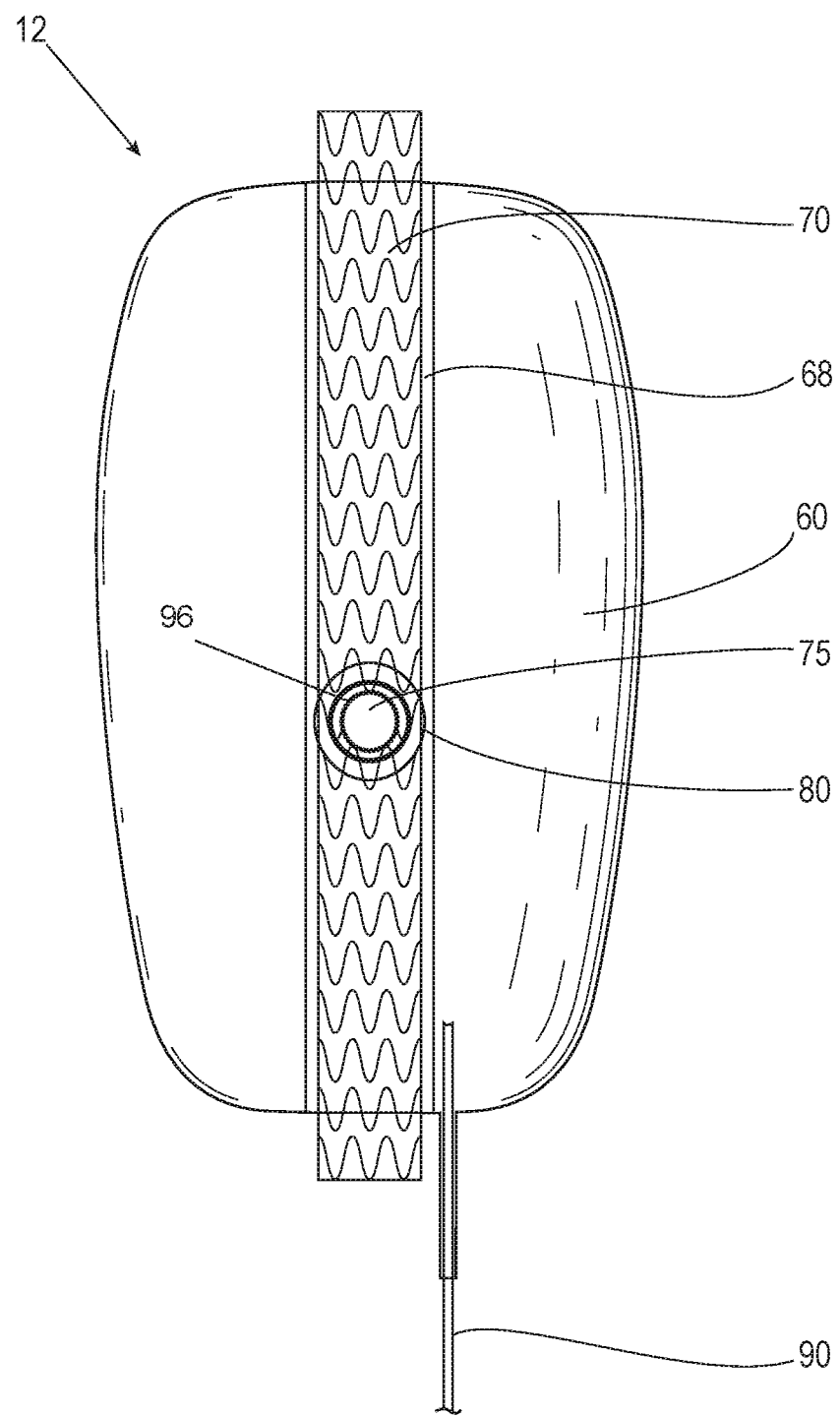
FIG. 11 illustrates another view of the system of FIG. 10 in accordance with an embodiment.
Figure 12:
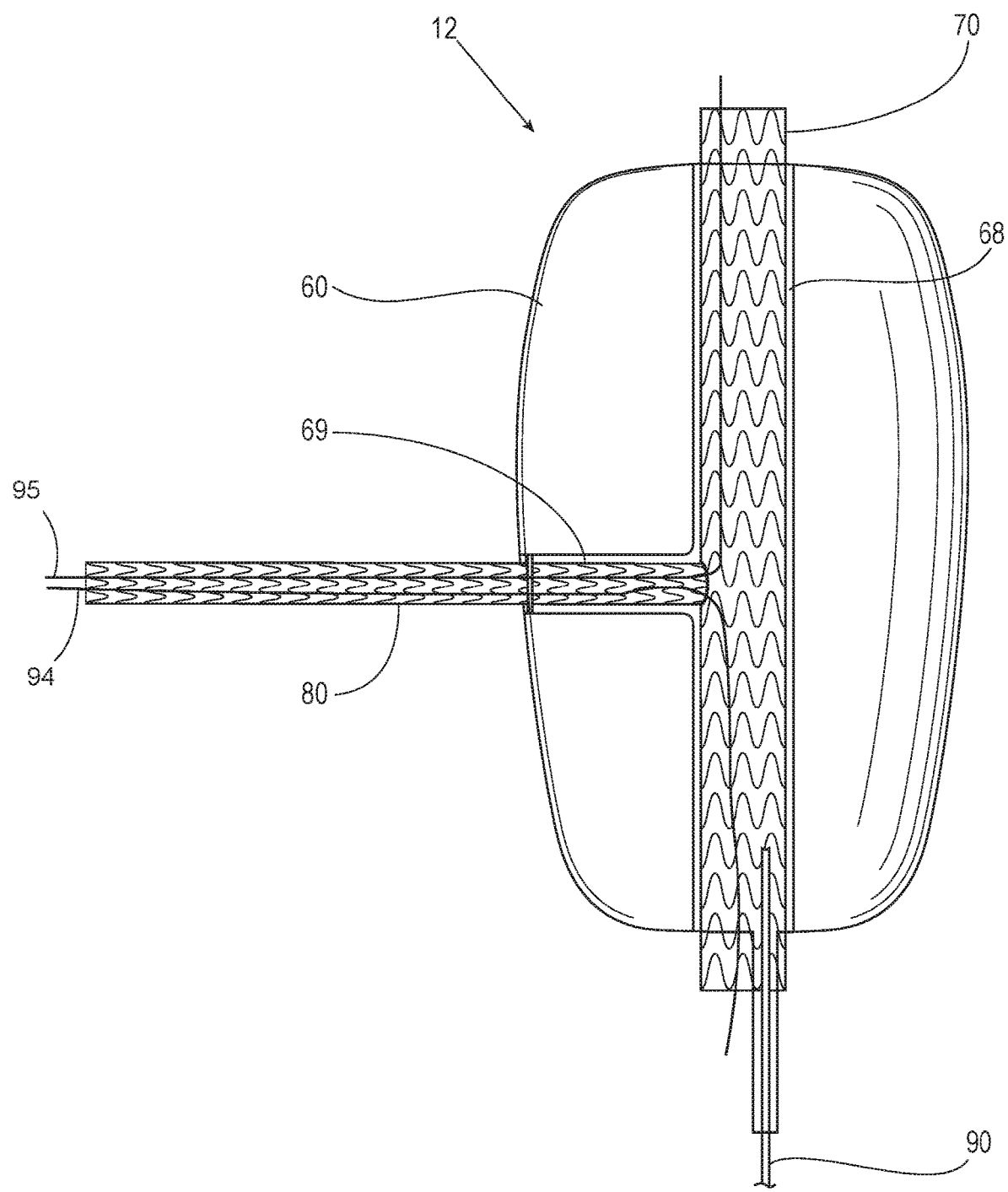
FIG. 12 illustrates yet another view of the system of FIG. 10 in accordance with an embodiment.

FIG. 10 illustrates the system 12 of FIG. 9 in accordance with an embodiment. FIG. 11 illustrates another view of the system 12 of FIG. 10 in accordance with an embodiment. FIG. 12 illustrates yet another view of the system 12 of FIG. 10 in accordance with an embodiment including wires 94 and 95. With reference to FIGS. 9, 10, 11, and 12, the system 12 includes a filling structure 60, a first scaffold 70, a second scaffold 80, and a fill tube 90. A first portion 61 of the filling structure 60 is configured and shaped to be located in at least a portion of the common iliac artery 3 upon deployment. A second portion 62 of the filling structure 60 is configured and shaped to be located in at least a portion of the external iliac artery 4 upon deployment. A portion 66 of an outer wall 67 of the filling structure 60 that is positionable to face the internal iliac artery 5 has an opening to allow the second scaffold 80 to access the internal iliac artery 5.

In various embodiments, upon deployment, a first end 64 of the filling structure 60 faces the aorta 1, and a second end 65 of the filling structure 60 is located in the external iliac artery 4, while the portion 66 of the outer wall 67 of the filling structure 60 faces the internal iliac artery 5. The filling structure 60 has the outer wall 67. In various embodiments, the filling structure 60 includes a first lumen 68 in the filling structure 60 that is defined by a first inner wall of the filling structure 60. Also, in various embodiments, the filling structure 60 includes a second lumen 69 in the filling structure 60 defined by a second inner wall of the filling structure 60.

The filling structure 60 is inflatable with a filling medium or material from an uninflated state to an inflated state. The first lumen 68 extends from the first end 64 of the filling structure 60 to the second end 65 of the filling structure 60. The second lumen 69 extends from a side of the first lumen 68 of the filling structure 60 to the portion 66 of the outer wall 67 of the filling structure 40. In various embodiments, the portion 66 of the outer wall 67 of the filling structure 60 is sized and configured to be positioned within the common iliac artery 3 after the system 12 has been deployed. In various embodiments, the filling structure 60 comprises an endobag with the first lumen 68 and the second lumen 69.

In some embodiments, the filling structure 60 is partially or completely formed from a generally noncompliant material. In some embodiments, the filling structure 60 is an expanded Polytetrafluoroethylene (ePTFE) sealed bag that is coated on the inside with polyurethane. An internal volume of the filling structure 60 is surrounded by the outer wall 67. In various embodiments, the first lumen 68 is cylindrically shaped with an open top and an open bottom. In various embodiments, the second lumen 69 is cylindrically shaped with an open top into the first lumen 68 and an open bottom.

In various embodiments, the filling structure 60 is fillable with a hardenable filling material such as Polyethylene glycol (PEG) or another polymer that may be polymerized in situ. In various embodiments, the filling structure 60 is fillable via the fill tube 90 that is detachable from the filling structure 60. In various embodiments, the filling structure 60 includes at least one valve at an end of the fill tube 90 to permit the introduction of the filling material or medium into the internal volume of the filling structure 60. In various embodiments, the valve is a simple flap valve. Other more complex ball valves, and other one-way valve structures may be provided. In other instances, two-way valve structures may be provided to permit both filling and selective emptying of the internal volume of the filling structure 60. In some instances, the fill tube 90 comprises a needle or other filling element to pass through a valve to permit both filling and removal of filling medium from the filling structure 60.

In some embodiments, various internal and external surfaces of the filling structure 60 are shaped, coated, treated, or otherwise modified, to provide for a number of particular features. For example, in some embodiments, the outer wall 67 is shaped to have rings, stipples, or other surface features formed into the material of the filling structure 60 at the time of molding, vapor deposition, or other manufacturing process. In some embodiments, an outer surface of the outer wall 67 is coated with one or more materials, such as adhesives, drugs, active substances, fibers, flocking, foams, or a variety of other materials. Such surface features or modifications allow for enhancing sealing or attachment of the outer wall 67 to an inner surface of a blood vessel being treated. In various embodiments, upon inflation of the filling structure 60 with the filling medium, the outer wall 67 expands to contact surfaces of one or more blood vessels.

In various embodiments, an inner surface of the outer wall 67 of the filling structure 60 is modified by providing features, coatings, surface roughening, or a variety of other modifications. Such internal features allow for enhancing adherence of the inner surface of the outer wall 67 to the filling material or medium as the filling medium is cured or otherwise hardened in the internal volume of the filling structure 60. In some instances, materials may be coated on all or a portion of the inside surface of the outer wall 67 to induce or catalyze hardening of the filling medium as it is being introduced into the filling structure 60.

In various embodiments, the first scaffold 70 comprises a stent 71 and a graft 72, such that it is a stent graft. The first scaffold 70 has a first end 73 and a second end 74. The first scaffold 70 also has a fenestration 75 in the stent 71 and graft 72 of the first scaffold 70 to allow for insertion of the second scaffold 80. In various embodiments, the first scaffold 70 has a cylindrical shape with an open top and an open bottom to form a lumen. In various embodiments, the first scaffold 70 is attached to an inner surface of the first lumen 68 of the filling structure 60. In some embodiments, the first scaffold 70 comprises the stent 71 and, in some embodiments, the first scaffold 70 comprises the stent 71 with the graft 72 covering the stent 71. In some embodiments, the stent 71 is made from cobalt-chromium (CoCr) alloy, stainless steel, nitinol, or the like, and in some embodiments the graft 72 comprises a polymer cover, such as ePTFE, or the like, that is applied to the stent 71 as the graft 72.

In various embodiments, the second scaffold 80 comprises a stent 81 and a graft 82, such that it is a stent graft. The second scaffold 80 has a first end 83 and a second end 84. In various embodiments, the second scaffold 80 has a cylindrical shape with an open top and an open bottom to form a lumen. The filling structure 60 is inflatable or expandable, and when it expands, the second lumen 69 is revealed. In various embodiments, the second scaffold 80 is positionable within the second lumen 69 of the filling structure 60 to extend from the fenestration 75 in the first scaffold 70 though the second lumen 69 and out into the internal iliac artery 5. In various embodiments, the filling structure 60 does not extend into the internal iliac artery 5 but the second scaffold 80 is long enough to extend out of the second lumen 69 and into the internal iliac artery 5. In some embodiments, the second scaffold 80 comprises the stent 81 and, in some embodiments, the second scaffold 80 comprises the stent 81 with the graft 82 covering the stent 81. In some embodiments, the stent 81 is made from cobalt-chromium (CoCr) alloy, stainless steel, nitinol, or the like, and in some embodiments the graft 82 comprises a polymer cover, such as ePTFE, or the like, that is applied to the stent 81 as the graft 82.

In various embodiments, the filling structure 60 and/or the first scaffold 70 further includes a radiopaque marker 96 and the one or more wires 94, 95. In various embodiments, the radiopaque marker 96 is assembled next to the fenestration 75 of the first scaffold 70 to aid in locating the fenestration 75 and the second lumen 69 for insertion of the second scaffold 80 when the filling structure 60 is in the body of a patient. The radiopaque marker 96 in various embodiments indicates a location of the fenestration 75. In some embodiments, the radiopaque marker 96 is a thin-walled metal tube providing for visibility under an x-ray fluoroscope and is made from a high density metal, such as platinum, gold, tantalum, or the like. In some embodiments, the second lumen 69 and/or the fenestration 75 is pre-wired with the one or more wires 94, 95, such as a pre-cannulated wire through the fenestration 75 that is positionable within the internal iliac artery 5 with the use of precurved or steerable catheters. In some embodiments, the positioning of the wire 94 is performed via access through the ipsilateral side from the external iliac artery 4. In some embodiments, the positioning of the wire 95 is performed via access through the contralateral side by going over the aortic bifurcation 2. In various embodiments, the anatomy of the patient would determine the approach as to whether to access through the ipsilateral or contralateral side. In some embodiments there are the two pre-cannulated wires 94, 95 going in opposite directions from the fenestration 75 to accommodate both approaches. In such embodiments, the wire not being used could simply be removed prior to putting the system 12 in the patient.

A method for deploying the system 12 includes inserting a guide wire through a puncture in the patient's groin to access the external iliac artery 4 and to move the guide wire up through the common iliac artery 3. In various embodiments, a delivery catheter is used to deliver the filling structure 60 with the first scaffold 70 that is attached to the inner surface of the first lumen 68 of the filling structure 60. In various embodiments, the catheter includes a catheter shaft with a balloon near its distal end. In some embodiments, the first scaffold 70, which is radially expandable, is positioned over the balloon, and the filling structure 60 is disposed over the first scaffold 70 since the first scaffold 70 is located within the first lumen 68. In some embodiments, the first scaffold 70 is self-expandable and there is no need for a separate balloon for expansion. In various embodiments, the catheter further comprises a guide wire lumen for following the guide wire. In various embodiments, the catheter is also connected to the fill tube 90 for delivering a filling medium or material to the internal volume of the filling structure 60.

In various embodiments, the balloon is initially in an uninflated state. The first scaffold 70 is initially in an unexpanded state on the balloon. The filling structure 60 is initially in an uninflated state with the first scaffold 70 in the unexpanded state at least partially within the first lumen 68. In various embodiments, the catheter with the filling structure 60 in the uninflated state and the first scaffold 70 in the unexpanded state is advanced over the guide wire. In some embodiments, the first scaffold 70 is self-expandable, and rather than using a balloon, the catheter includes a sheath to surround the first scaffold 70 and the filling structure 60, and the sheath can be retracted to allow for the first scaffold 70 to expand.

In various embodiments, the system 12 includes a pre-cannulated wire through the window or fenestration 75 in the first scaffold 70 at the branch, and the fenestration 75 is positionable toward the internal iliac artery 5. In various embodiments of the method for deployment, the wire is placed into the internal iliac artery 5 with the use of pre-curved or steerable catheters. In some embodiments, the positioning of the wire is performed via access through the ipsilateral side from the external iliac artery 4. In some embodiments, the positioning of the wire is performed via access through the contralateral side by going over the aortic bifurcation 2. In various embodiments, the anatomy of the patient would determine the approach as to whether to access through the ipsilateral or contralateral side.

In various embodiments, once the internal iliac artery 5 is cannulated, a sheath is placed into the internal iliac artery 5. Then in various embodiments the second scaffold 80 is tracked to the target location that is at least partially in the internal iliac artery 5 by passing through the fenestration 75 in the first scaffold 70 to position the second scaffold 80 partially in the second lumen 69 of the filling structure 60. For a balloon expandable system 12, in various embodiments the second scaffold 80 surrounds a second balloon and the balloons would all be inflated using a kissing balloon technique. In various embodiments, the balloons protect and preserve the first lumen 68 and the second lumen 69 during filling of the filling structure 60. In various embodiments, the stent 71 and the stent 81 are made with enough radial force to withstand the fill pressures of the filling structure 60 such that balloons are not necessary for deployment.

In various embodiments, the method of deployment further includes pre-fill of the filling structure 60, such as with a saline solution, and then evacuation of the saline solution, and then polymer fill of an interior volume of the filling structure 60. In some embodiments, an optional secondary fill of the filling structure 60 is performed. In some embodiments, the fill tube 90 for the filling structure 60 has a "pipe cleaner" that is removable and insertable multiple times to allow for more than two fillings of the filling structure 60. In various embodiments, the saline solution can be introduced into the internal volume of the filling structure 60 through the fill tube 90 to unfurl the filling structure 60. The saline solution can then be withdrawn through the fill tube 90, and the filling structure 60 is filled with a hardenable filling medium or material such as PEG or another polymer that may be polymerized in situ. In various embodiments, the filling medium is able to cure or harden in place. It may be desirable to monitor pressure of the filling medium or material as it fills the filling structure 60 and/or the volume of filling medium or material introduced into the filling structure 60. The hardenable filling medium is used to fill the filling structure 60 to cause an outer surface of the filling structure 60 to expand and create a seal with an inner surface of one or more blood vessels.

Any balloons can then be deflated and removed along with the catheter shaft and the guide wire, which opens a lumen through the first scaffold 70 to allow for blood to flow from the aorta 1 through the first scaffold 70 to the external iliac artery 4. A lumen is also open through the second scaffold 80 to allow blood to flow from the aorta 1, through a portion of the first scaffold 70, through the fenestration 75 in the first scaffold 70, and through the second scaffold 80 to the internal iliac artery 5.

In various embodiments, upon deployment, the first portion 61 of the filling structure 60 is located in at least a portion of the common iliac artery 3, and the second portion 62 of the filling structure 60 is located in at least a portion of the external iliac artery 4, while the portion 66 of the outer wall 67 of the filling structure 60 remains in the common iliac artery 3. Also, upon deployment in various embodiments, the first end 73 of the first scaffold 70 is positioned to accept blood from the aorta 1, the second end 74 of the first scaffold 70 is positioned in the external iliac artery 4 to deliver blood to the external iliac artery 4, the fenestration 75 of the first scaffold 70 faces the internal iliac artery 5, the first end 83 of the second scaffold 80 is positioned within the fenestration 75 of the first scaffold 70, and the second end 84 of the second scaffold 80 is positioned in the internal iliac artery 5 to deliver blood to the internal iliac artery 5.

Figure 13:
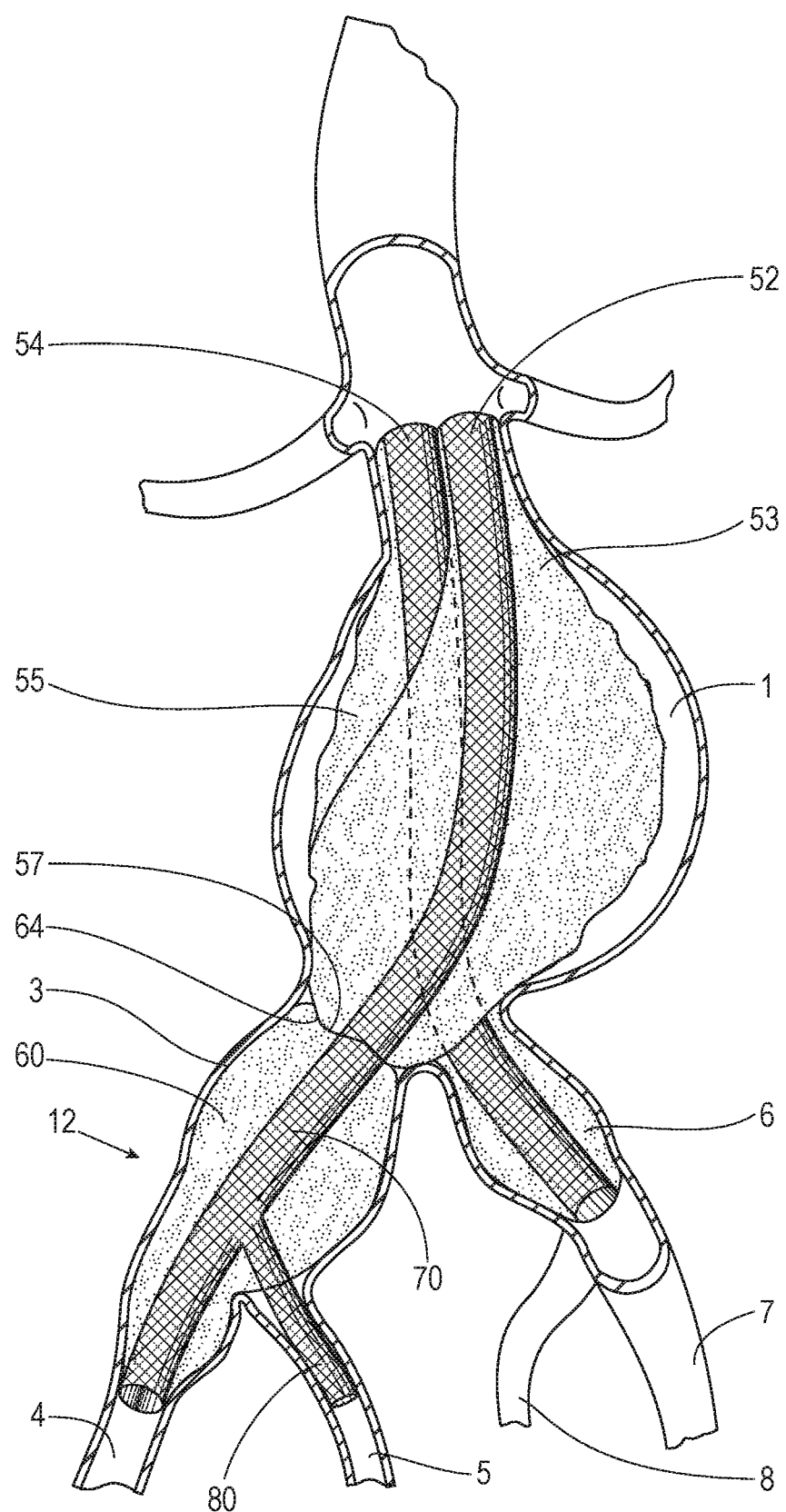
FIG. 13 illustrates an example deployment of the system of FIG. 9 in accordance with an embodiment that interfaces with another system to seal an aneurysm.

With reference to FIG. 13, the system 12 with the filling structure 60, the first scaffold 70, and the second scaffold 80 can be used in various embodiments as an extender for another system used to repair an AAA in an aorta 1 with the scaffold 52, the filling structure 53, the scaffold 54, and the filling structure 55. In various embodiments, the system 12 is implanted in at least portions of the common iliac artery 3, the external iliac artery 4, and the internal iliac artery 5 to seal a portion of the aneurysm that extends down into the common iliac artery 3 and the external iliac artery 4 from the aorta 1. In various embodiments, a portion of the first scaffold 70 is mated with the scaffold 52 to allow for continuous blood flow from the scaffold 52 to the first scaffold 70. Also, in various embodiments, the first end 64 of the filling structure 60 abuts the end 57 of the filling structure 53.

FIG. 14A illustrates another view of the system of FIG. 10 in accordance with an embodiment. FIG. 14B illustrates a portion of the system of the FIG. 14A shown by a dotted circle in FIG. 14A. FIG. 15A illustrates another view of the system of FIG. 10 in accordance with an embodiment. FIG. 15B illustrates a portion of the system of the FIG. 15A shown by a dotted circle in FIG. 15A. With reference to FIGS. 14A, 14B, 15A, and 15B, in various embodiments, the fenestration 75 in the first scaffold 70 is larger than an expanded diameter of the second scaffold 80. In some embodiments, the fenestration 75 in the first scaffold 70 has a greater length than an expanded diameter of the second scaffold 80. In some embodiments, the fenestration 75 in the first scaffold 70 has a greater length and a greater width than an expanded diameter of the second scaffold 80. In various embodiments, after the second scaffold 80 has expanded, any remaining opening in the fenestration 75 of the first scaffold 70 that is outside of the second scaffold 80 is filled by a portion 98 of the filling structure 60 when the filling structure 60 is filled with a filling medium. Having a larger fenestration 75 may allow for easier insertion and positioning of the second scaffold 80, and having the portion 98 of the filling structure 60 fill any remaining gaps in the fenestration 75 provides for a tight seal to prevent leakage of blood around an outside of the second scaffold 80.

Figure 16:
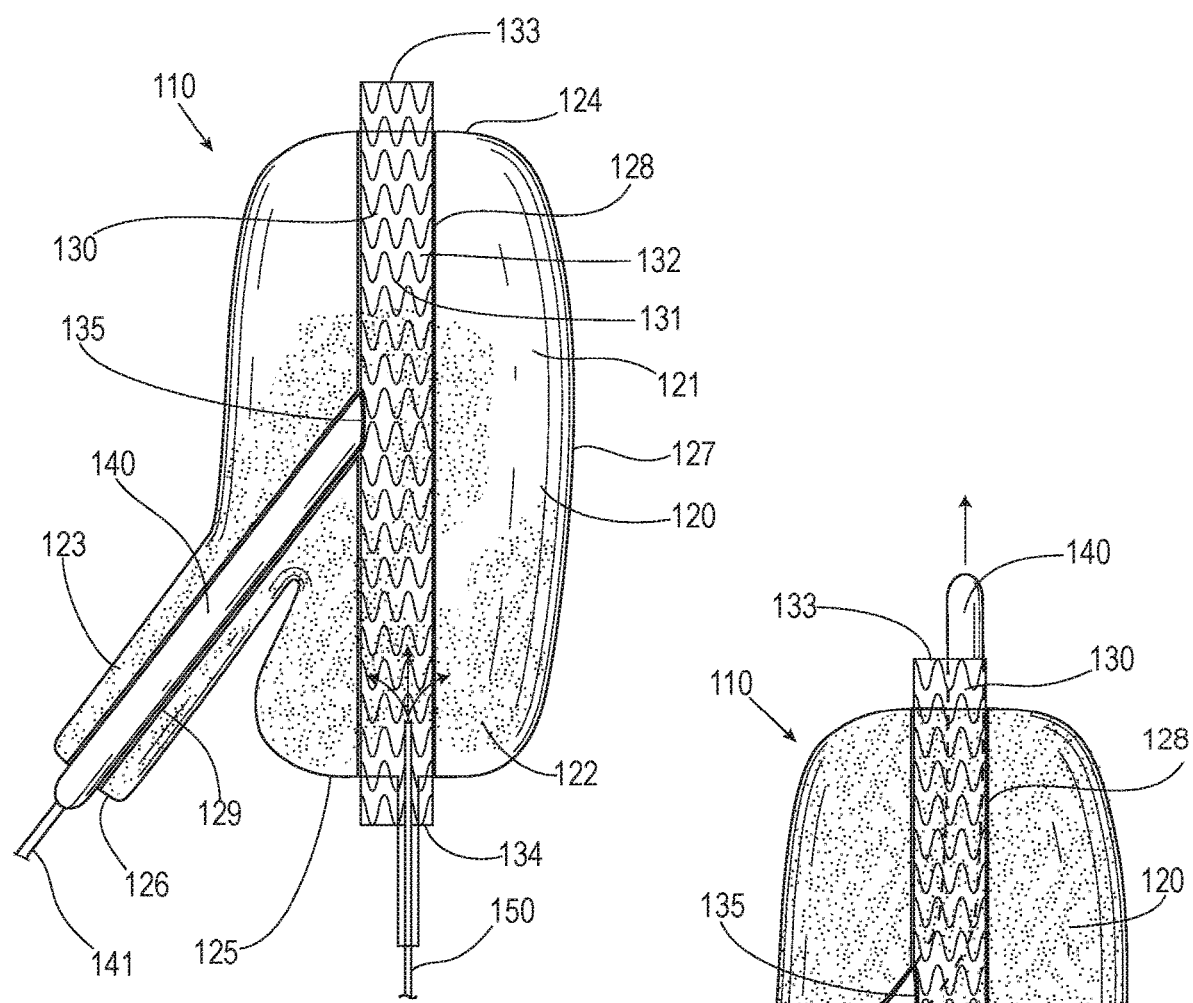
FIG. 16 illustrates a system in accordance with an embodiment including a filling structure having a portion that is expandable into at least a portion of an internal iliac artery.
Figure 17:
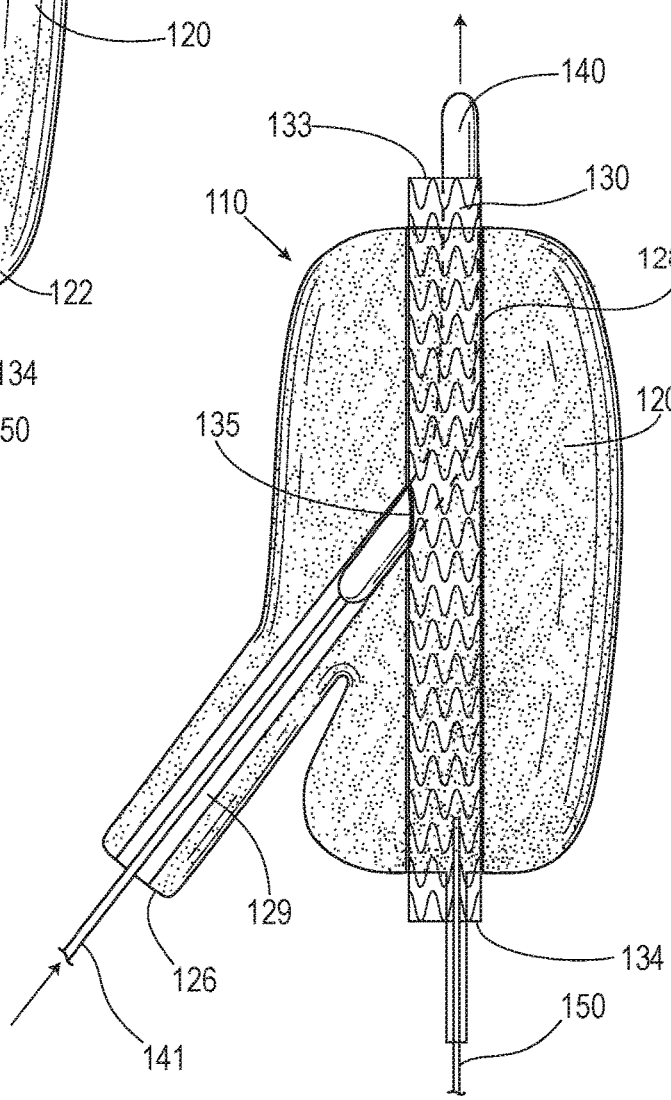
FIG. 17 illustrates the system of FIG. 16 in accordance with an embodiment in which a balloon is removable from a lumen in a filling structure after the filling structure has been filled with a hardenable material to provide the lumen in the filling structure for allowing for blood flow to an internal iliac artery.

FIGS. 16 and 17 illustrate a system 110 in accordance with an embodiment that is deployable in at least portions of a common iliac artery, an external iliac artery, and an internal iliac artery to seal at least a portion of an aneurysm. In various embodiments, the device or system 110 allows for sealing at least a portion of an aneurysm in at least portions of the common iliac artery, the external iliac artery, and the internal iliac artery. The system 110 includes a filling structure 120, a first scaffold 130, and a fill tube 150. A first portion 121 of the filling structure 120 is configured and shaped to be located in at least a portion of the common iliac artery upon deployment. A second portion 122 of the filling structure 120 is configured and shaped to be located in at least a portion of the external iliac artery upon deployment. A third portion 123 of the filling structure 120 is configured and shaped to be located in at least a portion of the internal iliac artery upon deployment.

In various embodiments, upon deployment, a first end 124 of the filling structure 120 faces the aorta, a second end 125 of the filling structure 120 is located in the external iliac artery, and a third end 126 of the filling structure 120 is located in the internal iliac artery. The filling structure 120 has an outer wall 127. In various embodiments, the filling structure 120 includes a first lumen 128 in the filling structure 120 that is defined by a first inner wall of the filling structure 120. Also, in various embodiments, the filling structure 120 includes a second lumen 129 in the filling structure 120 defined by a second inner wall of the filling structure 120.

In various embodiments, the first scaffold 130 comprises a stent 131 and a graft 132, such that it is a stent graft. The first scaffold 130 has a first end 133 and a second end 134. The first scaffold 130 also has a fenestration 135 in the stent 131 and graft 132 of the first scaffold 130 to allow for blood to flow through the second lumen 129 of the filling structure 120. In various embodiments, the first scaffold 130 has a cylindrical shape with an open top and an open bottom to form a lumen. In various embodiments, the first scaffold 130 is attached to an inner surface of the first lumen 128 of the filling structure 120. In some embodiments, the first scaffold 130 comprises the stent 131 and, in some embodiments, the first scaffold 130 comprises the stent 131 with the graft 132 covering the stent 131. In some embodiments, the stent 131 is made from cobalt-chromium (CoCr) alloy, stainless steel, nitinol, or the like, and in some embodiments the graft 132 comprises a polymer cover, such as ePTFE, or the like, that is applied to the stent 131 as the graft 132.

In various embodiments, the system 110 of FIGS. 16 and 17 is similar to the system 10 of FIG. 4 except that rather than have the second scaffold 40, the system 110 just uses the second lumen 129 of the filling structure 120 to allow for blood flow to the internal iliac artery. Thus, the explanation of the method of deployment of the system 10 discussed above also applies for the system 110 except for the deployment of the second scaffold 40. Instead of deploying the second scaffold 40, during deployment of the system 110, a balloon 140 on a guide wire 141 is inflated within the second lumen 129 of the filling structure 120 and the filling structure 120 is filled with the filling medium that hardens to define the second lumen 129. The balloon 140 is then removed as shown in FIG. 17 while the second lumen 129 remains defined to allow for blood flow from the fenestration in the first scaffold 130 to the internal iliac artery.

Figure 18A:
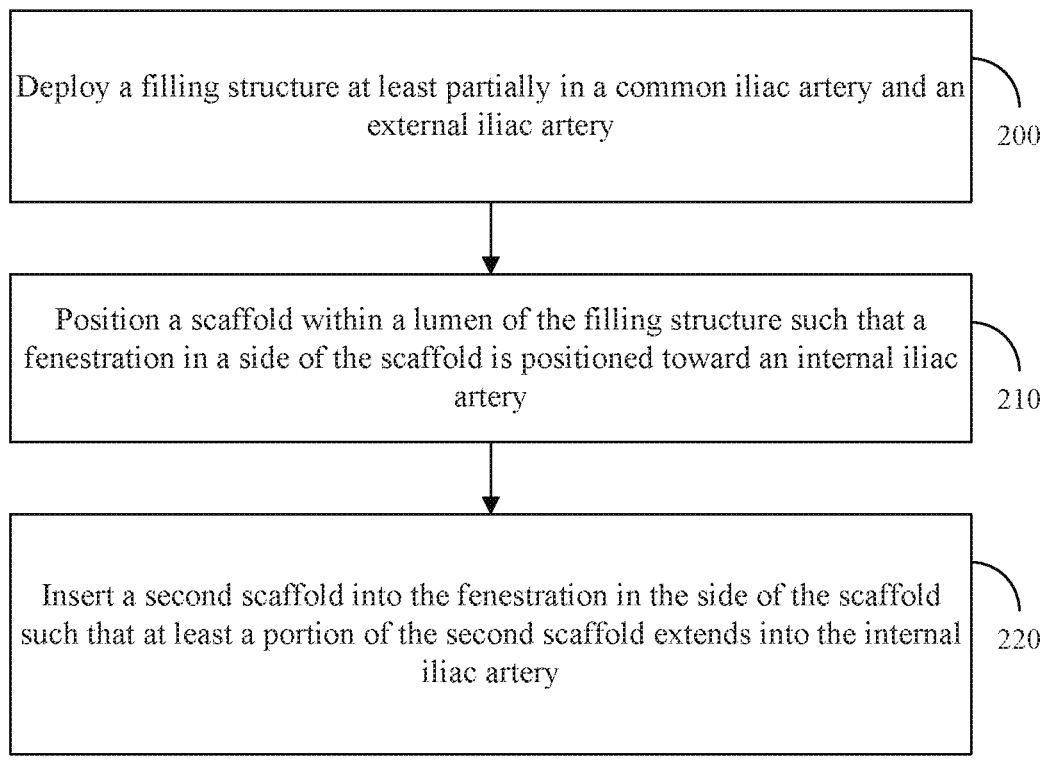
FIG. 18A illustrates a flowchart of a method in accordance with an embodiment.

FIG. 18A illustrates a flowchart of a method in accordance with an embodiment. In step 200, a filling structure is deployed at least partially in a common iliac artery and an external iliac artery. In step 210, a scaffold is positioned within a lumen of the filling structure such that a fenestration in a side of the scaffold is positioned toward an internal iliac artery. In some embodiments, the scaffold is attached inside the lumen of the filling structure prior to deployment of the filling structure. In step 220, a second scaffold is inserted into the fenestration in the side of the scaffold such that at least a portion of the second scaffold extends into the internal iliac artery. In various embodiments, upon deployment of the filling structure, a first portion of the filling structure is located in at least a portion of the common iliac artery, a second portion of the filling structure is located in at least a portion of the external iliac artery, and a third portion of the filling structure is located in at least a portion of the internal iliac artery.

Figure 18B:
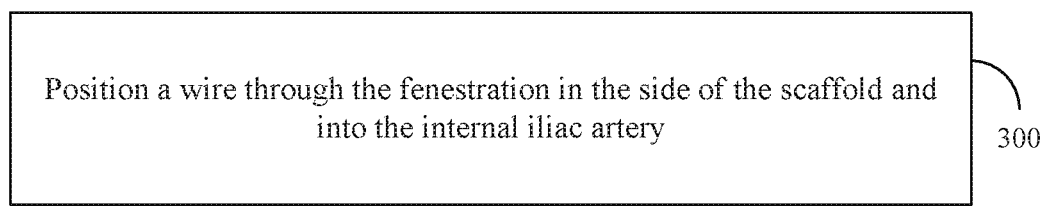
FIG. 18B illustrates a step that can be used with the method of FIG. 18A.

FIG. 18B illustrates a step that can be used with the method of FIG. 18A. In step 300, a wire is positioned through the fenestration in the side of the scaffold and into the internal iliac artery. In various embodiments, the positioning of the wire is performed by a catheter passing over an aortic bifurcation.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention.

What is claimed is:

1. A system, comprising:
a filling structure deployable at least partially in a common iliac artery and an external iliac artery;
wherein the filling structure has a first lumen and a second lumen, the second lumen extending from the first lumen in the filling structure and configured to be positioned toward an internal iliac artery; and
a scaffold positionable within the first lumen of the filling structure, the scaffold having a fenestration in a side of the scaffold that is configured to be positioned toward an internal iliac artery.

2. The system of claim 1, further comprising:
a second scaffold configured to be positioned within the second lumen.

3. The system of claim 2,
wherein the second scaffold is configured to be inserted into the fenestration in the side of the scaffold.

4. The system of claim 1,
wherein a first portion of the filling structure is configured to be located in at least a portion of the common iliac artery upon deployment of the filling structure;
wherein a second portion of the filling structure is configured to be located in at least a portion of the external iliac artery upon deployment of the filling structure; and
wherein a third portion of the filling structure is configured to be located in at least a portion of the internal iliac artery upon deployment of the filling structure.

5. The system of claim 1,
wherein the first lumen of the filling structure extends from a first end of the filling structure that is positionable to face an aorta to a second end of the filling structure that is positionable in the external iliac artery.

6. The system of claim 5,
wherein the second lumen of the filling structure extends from a side of the first lumen of the filling structure to a third end of the filling structure that is configured to be positioned in the internal iliac artery.

7. The system of claim 1,
wherein the fillable structure is configured to be inflated with a filling medium.

8. The system of claim 3,
wherein the fenestration in the side of the scaffold is larger than an expanded diameter of the second scaffold.

9. The system of claim 8,
wherein the filling structure is expandable to provide a seal around the second scaffold when the second scaffold is located within the fenestration in the side of the scaffold and the filling structure is inflated with a filling medium.

10. The system of claim 1,
wherein the scaffold is attached to an inner surface of the first lumen.

11. The system of claim 1,
wherein a length of a second scaffold that is configured to be inserted into the fenestration in the side of the scaffold has a length that is greater than a length of the second lumen.

12. The system of claim 1, further comprising:
a radiopaque marker located next to the fenestration of the scaffold.

13. The system of claim 1, further comprising:
a wire configured to extend through the fenestration in the side of the scaffold to the internal iliac artery.

14. The system of claim 1, further comprising:
a balloon that is configured to be inflated within the second lumen of the filling structure and that is removable from the second lumen.

15. A method, comprising:
deploying a filling structure at least partially in a common iliac artery and an external iliac artery;
wherein the filling structure has a first lumen and a second lumen therein, the second lumen extending from the first lumen in the filling structure;
positioning the second lumen toward an internal iliac artery; and
positioning a scaffold within the first lumen of the filling structure such that a fenestration in a side of the scaffold is positioned toward an internal iliac artery
wherein the fenestration is configured to receive a second scaffold.

16. The method of claim 15, further comprising:
inserting a second scaffold into the fenestration in the side of the scaffold such that at least a portion of the second scaffold extends into the internal iliac artery.

17. The method of claim 15,
wherein, upon deployment of the filling structure, a first portion of the filling structure is located in at least a portion of the common iliac artery, a second portion of the filling structure is located in at least a portion of the external iliac artery, and a third portion of the filling structure is located in at least a portion of the internal iliac artery.

18. The method of claim 15, further comprising:
positioning a wire through the fenestration in the side of the scaffold and into the internal iliac artery.

19. The method of claim 18,
wherein the positioning of the wire is performed by a catheter passing over an aortic bifurcation.

20. A system, comprising:
a filling structure that is bifurcated;
wherein the filling structure has a first lumen that extends from a first end to a second end of the filling structure; and
wherein the filling structure has a second lumen that extends from a side of the first lumen to a third end of the filling structure wherein a first scaffold positioned in the first lumen of the filling structure and having a fenestration in a side of the first scaffold that is positioned toward the second lumen of the filling structure.

21. The system of claim 20, further comprising:
a first scaffold positioned in the first lumen of the filling structure and having a fenestration in a side of the first scaffold that is positioned toward the second lumen of the filling structure; and
a second scaffold positioned in the second lumen of the filling structure and extending through the fenestration in the side of the first scaffold.

22. The system of claim 20,
wherein a first portion of the filling structure is configured to be located in at least a portion of a common iliac artery upon deployment of the filling structure;
wherein a second portion of the filling structure is configured to be located in at least a portion of an external iliac artery upon deployment of the filling structure; and
wherein a third portion of the filling structure is configured to be located in at least a portion of an internal iliac artery upon deployment of the filling structure.

23. The system of claim 1, wherein the filling structure comprises a single continuous volume from a first end to a second end of the filling structure.

24. The system of claim 1, wherein the filling structure comprises a volume, and the first and second lumen extend through said volume.

* * * * *